United States Patent [19]

Machii et al.

[11] Patent Number: 5,661,147

[45] Date of Patent: Aug. 26, 1997

[54] IMIDAZOQUINAZOLINE DERIVATIVES

[75] Inventors: Daisuke Machii; Kenji Matsuno; Iwao Kinoshita; Yuji Nomoto; Haruki Takai; Tetsuji Ohno; Ken Nagashima; Tomoko Ishikawa, all of Shizuoka-ken; Koji Yamada, Sagamihara; Michio Ichimura, Numazu; Hiroshi Kase, Koganei, all of Japan

[73] Assignee: Kyowa Hakko Kogyo Co., Ltd., Tokyo, Japan

[21] Appl. No.: 424,274

[22] PCT Filed: Sep. 2, 1994

[86] PCT No.: PCT/JP94/01456

§ 371 Date: Apr. 26, 1995

§ 102(e) Date: Apr. 26, 1995

[87] PCT Pub. No.: WO95/06648

PCT Pub. Date: Mar. 9, 1995

[30] Foreign Application Priority Data

Sep. 3, 1993 [JP] Japan ................. 5-219595

[51] Int. Cl.$^6$ .............. C07D 417/04; C07D 413/04; C07D 243/08; A61K 31/505

[52] U.S. Cl. .............. 514/218; 514/228.5; 514/232.8; 514/267; 540/575; 544/60; 544/115

[58] Field of Search .............. 544/234, 60, 115; 540/575; 514/267, 218, 232.8, 228.5

[56] References Cited

U.S. PATENT DOCUMENTS 4,954,498  9/1990  Mertens et al. ................. 514/254
5,569,658  10/1996  Barker ................. 514/250

FOREIGN PATENT DOCUMENTS 635507  1/1995  European Pat. Off. .

OTHER PUBLICATIONS

J. Med. Chem., vol. 29, No. 6 (1986) 972–77.

J. Med. Chem., vol. 32, No. 10 (1989) 2247–54.

J. Org. Chem., vol. 51, No. 5 (1986) 616–20.

*Primary Examiner*—Matthew V. Grumbling
*Attorney, Agent, or Firm*—Fitzpatrick, Cella, Harper & Scinto

[57] ABSTRACT

The present invention relates to imidazoquinazoline derivatives represented by the general formula (I):

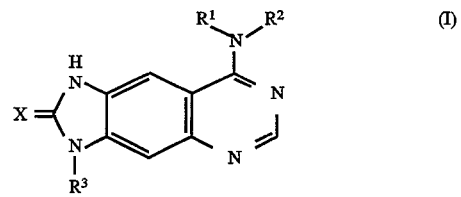

or pharmacologically acceptable salts thereof.

The compounds of the present invention have strong and selective cGMP-specific PDE inhibitory activity and are useful for treating or ameliorating cardiovascular diseases such as thrombosis, angina pectoris, hypertension, arterial sclerosis and the like, as well as asthma and the like.

8 Claims, No Drawings

IMIDAZOQUINAZOLINE DERIVATIVES

TECHNICAL FIELD

This is a 371 of PCT/JP94/01456, filed Sep. 2, 1994 from which priority is claimed.

The present invention relates to imidazoquinazoline derivatives or pharmacologically acceptable salts thereof which have the cyclic guanosine 3',5'-monophosphate (cGMP)-specific phosphodiesterase (PDE) inhibitory activity and are useful for treating or ameliorating cardiovascular diseases such as thrombosis, angina pectoris, hypertension, heart failure, arterial sclerosis and the like, as well as asthma and the like.

PRIOR ART cGMP plays an important role as a second messenger in intracellular signal transduction. An inhibitor of cGMP-specific PDE, an enzyme which degrades cGMP, increases the concentration of intracellular cGMP and enhances the effects of endothelium-derived relaxing factor (EDRF), nitro vasodilator or atrial natriuretic peptide, and shows the anti-platelet activity, the anti-vasocontraction activity and the vasodilating activity and are useful for treating angina pectoris, hypertension, congestive heart failure, post-PTCA restenosis, peripheral vascular diseases, bronchitis, chronic asthma, allergic asthma, allergic gravedo, glaucoma, alimentary canal diseases such as irritable intestine syndrome and the like.

The PDE inhibitory activity and the adenosine receptor antagonistic activity of imidazo[4,5-g]quinazoline derivatives are described in J. Med. Chem., 29, 972 (1986), J. Med. Chem., 32, 2247 (1989), J. Org. Chem., 51, 616 (1986) and the references cited therein. However, these compounds are neither a particularly strong PDE inhibitor nor a selective cGMP-specific PDE inhibitor.

DISCLOSURE OF THE INVENTION

The present invention relates to imidazoquinazoline derivatives (hereinafter referred to as Compound (I); a compound having another compound number corresponds to the compound represented by the formula of the same number) represented by the formula (I):

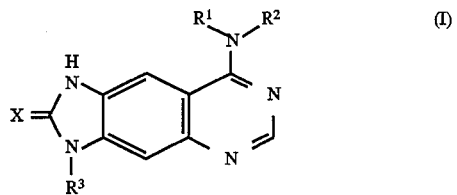

wherein $R^1$ and $R^2$ are the same or different and represent hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, bicycloalkyl, benzocycloalkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (which is optionally be substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl and where said alkyl part is optionally substituted with aryl), aromatic heterocycle group (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen, or trifluoromethyl), or $R^1$—N—$R^2$ represents heterocyclic group comprising nitrogen atom (which is optionally substituted with one to three substituents which are the same or different and are lower alkyl, aryl, or aralkyl), $R^3$ represents hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (where said aromatic heterocycle group part is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl, and where the alkyl part is optionally substituted with aryl), aromatic heterocycle group (where said aromatic heterocycle group is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen, or trifluoromethyl), and X represents oxygen atom or sulfur atom; or pharmacologically acceptable salts thereof.

In the definition of respective substituents in the formula (I), the examples of the alkyl and the alkyl part in lower alkyl, lower alkoxy, lower alkoxycarbonyl, and mono or dialkyl-substituted amino include straight or branched alkyls having 1 to 8 carbon atoms, for example, methyl, ethyl, propyl, isopropyl, butyl, isobutyl, sec-butyl, tert-butyl, pentyl, isopentyl, neopentyl, sec-pentyl, tert-pentyl, hexyl, isohexyl, heptyl, octyl, isooctyl and the like. The examples of cycloalkyl include cycloalkyls having 3 to 8 carbon atoms, for example, cyclopropyl, cyclobutyl, cyclopentyl, cyclohexyl, cycloheptyl, cyclooctyl and the like. The examples of bicycloalkyl include bicycloalkyls having 7 to 10 carbon atoms, for example, bicyclo[2.2.1]heptyl, bicyclo[2.2.2]octyl, bicyclo[3.3.1]nonyl and the like. The examples of benzocycloalkyl include benzocycloalkyls having 8 to 12 carbon atoms, for example, benzocyclobutyl, indanyl, benzocyclooctyl and the like. The examples of lower alkenyl include straight or branched alkenyls having 2 to 6 carbon atoms, for example, vinyl, allyl, propenyl, methacryl, butenyl, crotyl, pentenyl, hexenyl and the like. The examples of aralkyl include aralkyls having 7 to 15 carbon atoms, for example, benzyl, phenethyl, benzhydryl, naphthylmethyl and the like. The examples of aryl include phenyl, naphthyl and the like. The example of alicyclic heterocycle group include tetrahydrofuranyl, tetrahydropyranyl, pyrrolidinyl, piperidinyl, piperazinyl, homopiperazinyl, morpholinyl, thiomorpholinyl and the like. The examples of aromatic heterocycle group include pyridyl, pyrimidyl, quinolyl, isoquinolyl, thienyl, furyl, pyrrolyl, imidazolyl, benzothienyl, benzofuryl, indolyl and the like. The examples of heterocyclic group comprising nitrogen atom include pyrrolidinyl, piperidino, piperazinyl, morpholino, thiomorpholino, homopiperazinyl and the like. Halogen means fluorine, chlorine, bromine or iodine atom.

The examples of the pharmacologically acceptable salts of Compound (I) are pharmacologically acceptable acid addition salts, for example, inorganic acids such as hydrochloride, hydrobromide, hydroiodide, nitrate, sulfate, phosphate and the like, and organic acids such as formate, acetate, benzoate, tartrate, maleate, fumarate, succinate, oxalate, glyoxylate, aspartate, methanesulfonate, benzenesulfonate and the like.

Then, a process for preparing Compound (I) is described.

Process 1: Compound (Ia) wherein X is oxygen atom

Compound (Ia) can be prepared according to the following Reaction Scheme.

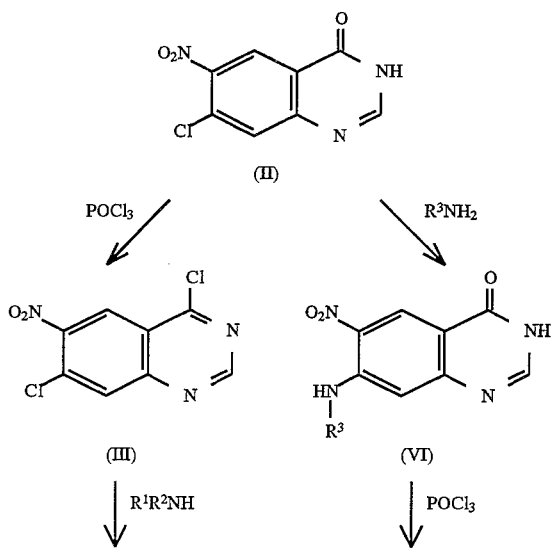

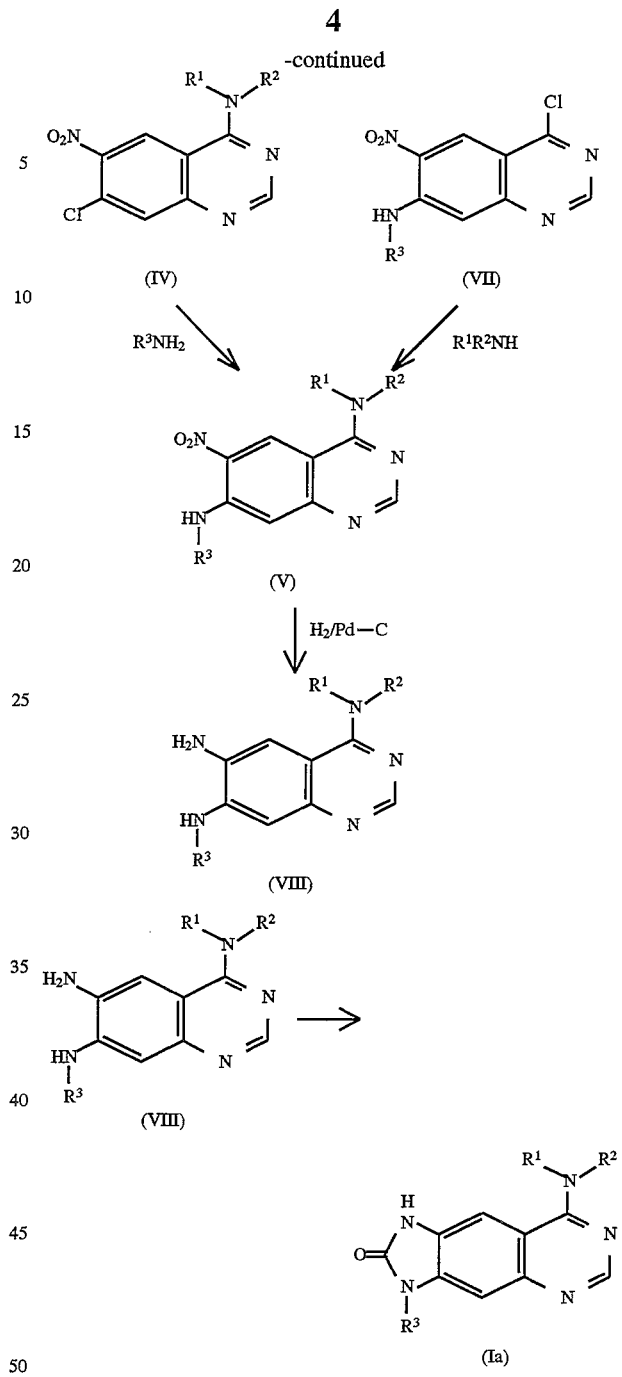

wherein $R^1$, $R^2$ and $R^3$ are as defined above.

Starting material Compound (II) can be prepared according to the known process [J. Org. Chem., 40, 356 (1975), etc.].

Dichloro compound (III) can be obtained by reacting Compound (II) with a chlorinating agent such as phosphorus oxychloride and the like at a temperature of room temperature to the boiling point of a solvent employed, in a solvent such as 1,2-dichloroethane or the like, or when no solvent is used, at a temperature of room temperature to the boiling point of a chlorinating agent employed, for 1 to 24 hours. Then, monoamino compound (IV) can be obtained by reacting Compound (III) with one equivalent to excess amount of an amine represented by the formula $R^1R^2NH$ (wherein $R^1$ and $R^2$ are as defined above), if necessary, in the presence of a base such as triethylamine or the like, in a solvent such as tetrahydrofuran or the like, at a temperature of −20° C. to room temperature for 30 minutes to 24 hours. Further, diamino compound (V) can be obtained by reacting Compound (IV) with one equivalent to excess amount of an amine represented by the formula $R^3NH_2$ (wherein $R^3$ is as defined above) or a solution containing the amine, in a solvent such as ethanol, butanol or the like, if necessary, using a sealed container (in a sealed tube) at a temperature of room temperature to 150° C. for 1 to 24 hours. Alternatively, diamino compound (V) can be obtained via Compound (VI) and Compound (VII) starting from Compound (II) by changing the order of the above reactions.

Alternatively, Compound (V) can be obtained by reacting Compound (VII) with hydroxylamine such as 5-amino-1-pentanol or the like, halogenating the resulting hydroxy compound according to the conventional method, then adding a suitable amine thereto to react.

Triamino compound (VIII) can be obtained by catalytic reduction of Compound (V) in the presence of a catalyst such as palladium on carbon or the like in a solvent such as tetrahydrofuran, ethanol, dimethylformamide or the like under hydrogen atmosphere, or in the presence of a reducing agent such as iron/ferric chloride or the like in a solvent such as ethanol, water or the like, at a temperature of room temperature to the boiling point of a solvent employed.

Compound (Ia) can be obtained by cyclization of Compound (VIII) using not less than 1 equivalent of N,N'-carbonyldiimidazole, phosgene or the like, if necessary, in the presence of a base, in an inert solvent. The examples of the base are triethylamine, pyridine and the like. The examples of the inert solvent are water, alcohol (methanol, ethanol and the like), non-polar solvent (ethyl acetate, ether and the like), aprotic polar solvent (acetonitrile, dimethylformamide, dimethyl sulfoxide, tetrahydrofuran, dioxane and the like), halogenated hydrocarbon (dichloromethane, chloroform and the like). The reaction is completed in 10 minutes to 48 hours at a temperature of 0° C. to the boiling point of a solvent employed.

Process 2: Compound (Ib) wherein X is sulfur atom

Compound (Ib) can be prepared according to the following Reaction Scheme:

(VIII) →

(Ib)

wherein $R^1$, $R^2$ and $R^3$ are as defined above.

Compound (Ib) can be obtained by cyclization of Compound (VIII) using not less than 1 equivalent of N,N'-thiocarbonyldiimidazole, carbon disulfide, thiophosgene or the liked if necessary, in the presence of a base, in an inert solvent. The examples of the base and inert solvent are the same as those described for preparation of Compound (Ia). The reaction is completed in 10 minutes to 48 hours at a temperature of 0° C. to the boiling point of a solvent employed.

Reaction intermediates and final compounds in the above processes can be isolated and purified by conventional methods employed in organic synthetic chemistry, for example, filtration, extraction, washing, drying, concentration, recrystallization, and various chromatographies and the like. In addition, reaction intermediates may be subjected to the subsequent reaction without purification.

Among compounds (I), some may have a tautomer. The present invention includes all possible isomers and mixture thereof, including tautomers.

When a salt of Compound (I) is desired, if Compound (I) is obtained in the salt form, the salt Compound (I) may be purified as it is and, if Compound (I) is obtained in the free form, it may be dissolved or suspended in an appropriate solvent followed by addition of an acid thereto to form a salt, which may be isolated and purified.

Compound (I) and pharmacologically acceptable salts thereof can also be present in the form of adducts with water or various solvents. Such adducts are included within the scope of the present invention.

Particular compounds (I) obtained in the present invention are shown in Table 1.

TABLE 1-1

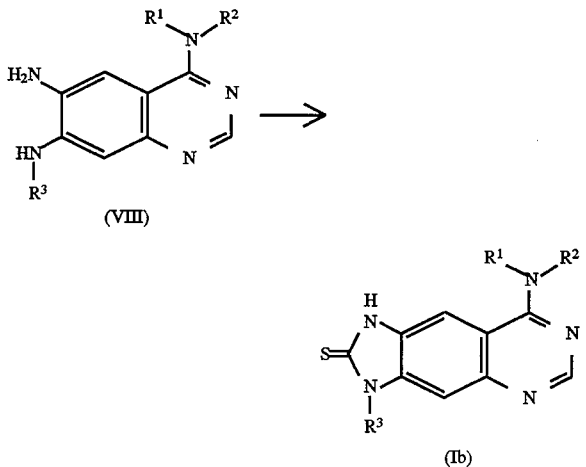

| Compound No. | X | $R^1$ | $R^2$ | $R^3$ |
|---|---|---|---|---|
| 1 | O | —CH$_2$—C$_6$H$_5$ | H | C$_2$H$_5$ |
| 2 | O | —CH$_2$—C$_6$H$_5$ | H | CH$_3$ |
| 3 | O | —CH$_2$—C$_6$H$_5$ | H | CH(CH$_3$)$_2$ |
| 4 | O | —CH$_2$—C$_6$H$_5$ | H | (CH$_2$)$_2$CH$_3$ |
| 5 | O | —CH$_2$—C$_6$H$_5$ | H | (CH$_2$)$_3$CH$_3$ |
| 6 | O | —CH$_2$—C$_6$H$_5$ | H | cyclopentyl |
| 7 | O | —CH$_2$—C$_6$H$_5$ | H | cyclohexyl |

TABLE 1-1-continued

[Structure: benzimidazole with X=, R³ on N, and C(=N-CH=N-)(NR¹R²) group]

| Compound No. | X | R¹ | R² | R³ |
|---|---|---|---|---|
| 8 | O | —CH₂—(phenyl) | H | cycloheptyl |
| 9 | O | —CH₂—(phenyl) | H | cyclooctyl |
| 10 | O | —CH₂—(phenyl) | H | —CH₂—(phenyl) |

TABLE 1-2

[Structure: benzimidazole with X=, R³ on N, and C(=N-CH=N-)(NR¹R²) group]

| Compound No. | X | R¹ | R² | R³ |
|---|---|---|---|---|
| 11 | O | —CH₂—(4-pyridyl) | H | C₂H₅ |
| 12 | O | —CH₂—(3-pyridyl) | H | C₂H₅ |
| 13 | O | —CH₂—(2-pyridyl) | H | C₂H₅ |
| 14 | O | —CH₂—(4-OCH₃-phenyl) | H | C₂H₅ |
| 15 | O | —CH₂—(3-OCH₃-phenyl) | H | C₂H₅ |

TABLE 1-2-continued

| Compound No. | X | R¹ | R² | R³ |
|---|---|---|---|---|
| 16 | O | —CH₂—(2-OCH₃-phenyl) | H | C₂H₅ |
| 17 | O | —CH₂—(4-CH₃-phenyl) | H | C₂H₅ |
| 18 | O | —CH₂—(3-CF₃-phenyl) | H | C₂H₅ |
| 19 | O | —CH₂—(4-F-phenyl) | H | C₂H₅ |
| 20 | O | —CH₂—(3,4-diF-phenyl) | H | C₂H₅ |

TABLE 1-3

[Structure: benzimidazole with X=, R³ on N, and C(=N-CH=N-)(NR¹R²) group]

| Compound No. | X | R¹ | R² | R³ |
|---|---|---|---|---|
| 21 | O | —CH₂—(4-Cl-phenyl) | H | C₂H₅ |
| 22 | O | —CH₂—(phenyl) | CH₃ | C₂H₅ |
| 23 | O | H | H | C₂H₅ |
| 24 | O | C₂H₅ | H | C₂H₅ |

TABLE 1-3-continued

[Structure: benzimidazole with X, R¹R²N-C=N-CH=N, R³]

| Compound No. | X | R¹ | R² | R³ |
|---|---|---|---|---|
| 25 | O | 2,3-dihydro-1H-inden-1-yl | H | C₂H₅ |
| 26 | O | phenyl | H | C₂H₅ |
| 27 | O | —(CH₂)₂—phenyl | H | C₂H₅ |
| 28 | O | —CH₂—(1-naphthyl) | H | C₂H₅ |
| 29 | O | —CH(phenyl)₂ | H | C₂H₅ |
| 30 | O | —CH₂—(tetrahydrofuran-2-yl) | H | C₂H₅ |

TABLE 1-4

[Structure: benzimidazole with X, R¹R²N-C=N-CH=N, R³]

| Compound No. | X | R¹ | R² | R³ |
|---|---|---|---|---|
| 31 | O | —(CH₂)₂—N(phenyl)—(CH₂)₂— | | C₂H₅ |
| 32 | O | —(CH₂)₂—N(CH₂-phenyl)—(CH₂)₂— | | C₂H₅ |
| 33 | O | —(CH₂)₂—CH(CH₂-phenyl)—(CH₂)₂— | | C₂H₅ |
| 34 | O | —(CH₂)₅— | | C₂H₅ |
| 35 | O | —(CH₂)₂—N(CH₃)₂ | CH₃ | C₂H₅ |
| 36 | O | —(CH₂)₃—N(CH₃)—(CH₂)₂— | | C₂H₅ |
| 37 | O | norbornyl | H | C₂H₅ |
| 38 | O | —CH₂—cyclohexyl | H | C₂H₅ |

TABLE 1-5

[Structure: benzimidazole with X, R¹R²N-C=N-CH=N, R³]

| Compound No. | X | R¹ | R² | R³ |
|---|---|---|---|---|
| 39 | S | —CH₂—phenyl | H | C₂H₅ |

TABLE 1-5-continued

[Structure: benzimidazole core with X=, R³ on N, NH, and side chain -C(=N-CH=N-)-N(R¹)(R²)]

| Compound No. | X | R¹ | R² | R³ |
|---|---|---|---|---|
| 40 | S | -CH₂-C₆H₅ | H | CH₃ |
| 41 | S | -CH₂-C₆H₅ | H | CH(CH₃)₂ |
| 42 | S | -CH₂-C₆H₅ | H | (CH₂)₂CH₃ |
| 43 | S | -CH₂-C₆H₅ | H | (CH₂)₃CH₃ |
| 44 | S | -CH₂-C₆H₅ | H | cyclohexyl |
| 45 | S | -CH₂-C₆H₅ | H | cycloheptyl |
| 46 | S | -CH₂-C₆H₅ | H | cyclooctyl |

TABLE 1-6

[Same core structure]

| Compound No. | X | R¹ | R² | R³ |
|---|---|---|---|---|
| 47 | S | -CH₂-(4-pyridyl) | H | C₂H₅ |
| 48 | S | -CH₂-(3-pyridyl) | H | C₂H₅ |
| 49 | S | -CH₂-(2-pyridyl) | H | C₂H₅ |
| 50 | S | -CH₂-C₆H₄-4-OCH₃ | H | C₂H₅ |
| 51 | S | -CH₂-C₆H₄-3-OCH₃ | H | C₂H₅ |
| 52 | S | -CH₂-C₆H₄-2-OCH₃ | H | C₂H₅ |
| 53 | S | -CH₂-C₆H₄-4-CH₃ | H | C₂H₅ |
| 54 | S | -CH₂-C₆H₄-3-CF₃ | H | C₂H₅ |
| 55 | S | -CH₂-C₆H₄-4-F | H | C₂H₅ |
| 56 | S | -CH₂-C₆H₃-3,4-F₂ | H | C₂H₅ |

TABLE 1-7

Structure: benzimidazole with X=, N-R³, and -C(=NR¹R²)=N-CH=N- (quinazoline-like fused)

| Compound No. | X | R¹ | R² | R³ |
|---|---|---|---|---|
| 57 | S | -CH₂-(4-Cl-C₆H₄) | H | C₂H₅ |
| 58 | S | -CH₂-C₆H₅ | CH₃ | C₂H₅ |
| 59 | S | H | H | C₂H₅ |
| 60 | S | C₂H₅ | H | C₂H₅ |
| 61 | S | 1-indanyl | H | C₂H₅ |
| 62 | S | C₆H₅ | H | C₂H₅ |
| 63 | S | -(CH₂)₂-C₆H₅ | H | C₂H₅ |
| 64 | S | -CH₂-(1-naphthyl) | H | C₂H₅ |
| 65 | S | -CH(C₆H₅)₂ | H | C₂H₅ |
| 66 | S | -CH₂-(tetrahydrofuran-2-yl) | H | C₂H₅ |

TABLE 1-8

| Compound No. | X | R¹ | R² | R³ |
|---|---|---|---|---|
| 67 | S | -CH₂-(thiophen-2-yl) | H | C₂H₅ |
| 68 | S | -(CH₂)₂-N(C₆H₅)-(CH₂)₂- | | C₂H₅ |
| 69 | S | -(CH₂)₂-N(CH₂C₆H₅)-(CH₂)₂- | | C₂H₅ |
| 70 | S | -(CH₂)₂-CH(CH₂C₆H₅)-(CH₂)₂- | | C₂H₅ |
| 71 | S | -(CH₂)₅- | | C₂H₅ |
| 72 | S | -(CH₂)₂-N(CH₃)₂ | CH₃ | C₂H₅ |
| 73 | S | -(CH₂)₃-N(CH₃)-(CH₂)₂- | | C₂H₅ |
| 74 | S | norbornyl | H | C₂H₅ |
| 75 | S | -CH₂-cyclohexyl | H | C₂H₅ |

TABLE 1-9

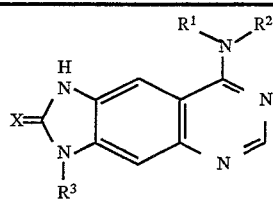

| Compound No. | X | R¹ | R² | R³ |
|---|---|---|---|---|
| 76 | O | —(CH$_2$)$_3$—N(morpholine) | H | C$_2$H$_5$ |
| 77 | O | —(CH$_2$)$_2$—N(morpholine) | H | C$_2$H$_5$ |
| 78 | O | —(CH$_2$)$_2$-(3-pyridyl) | H | C$_2$H$_5$ |
| 79 | O | —(CH$_2$)$_2$-(2-pyridyl) | H | C$_2$H$_5$ |
| 80 | O | —(CH$_2$)$_2$-(4-pyridyl) | H | C$_2$H$_5$ |
| 81 | O | —(CH$_2$)$_2$—N(pyrrolidine) | H | C$_2$H$_5$ |
| 82 | O | —(CH$_2$)$_2$—N(piperidine) | H | C$_2$H$_5$ |
| 83 | O | —CH$_2$—C$_6$H$_4$—N(CH$_3$)$_2$ | H | C$_2$H$_5$ |

TABLE 1-10

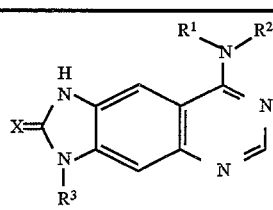

| Compound No. | X | R¹ | R² | R³ |
|---|---|---|---|---|
| 84 | O | —CH(C$_6$H$_5$)-(2-pyridyl) | H | C$_2$H$_5$ |

TABLE 1-10-continued

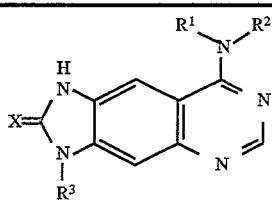

| Compound No. | X | R¹ | R² | R³ |
|---|---|---|---|---|
| 85 | O | —CH(CH$_3$)-(2-pyridyl) | H | C$_2$H$_5$ |
| 86 | O | —CH(CH$_3$)-(3-pyridyl) | H | C$_2$H$_5$ |
| 87 | O | —(CH$_2$)$_3$—N(piperazine)-N-(2-pyridyl) | H | C$_2$H$_5$ |
| 88 | O | —(CH$_2$)$_4$—N(morpholine) | H | C$_2$H$_5$ |
| 89 | O | —(CH$_2$)$_2$—N(2-methylpiperidine) | H | C$_2$H$_5$ |

TABLE 1-11

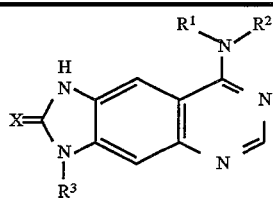

| Compound No. | X | R¹ | R² | R³ |
|---|---|---|---|---|
| 90 | S | —(CH$_2$)$_3$—N(morpholine) | H | C$_2$H$_5$ |
| 91 | S | —(CH$_2$)$_2$—N(morpholine) | H | C$_2$H$_5$ |
| 92 | S | —(CH$_2$)$_2$-(3-pyridyl) | H | C$_2$H$_5$ |
| 93 | S | —(CH$_2$)$_2$-(2-pyridyl) | H | C$_2$H$_5$ |

TABLE 1-11-continued

Structure: benzimidazole (X=on C2, NH and N-R³) fused, with -N(R¹)(R²) substituent on pyrimidine ring.

| Compound No. | X | R¹ | R² | R³ |
|---|---|---|---|---|
| 94 | S | -(CH₂)₂-(4-pyridyl) | H | C₂H₅ |
| 95 | S | -(CH₂)₂-N(pyrrolidinyl) | H | C₂H₅ |
| 96 | S | -(CH₂)₂-N(piperidinyl) | H | C₂H₅ |
| 97 | S | -CH₂-(4-N(CH₃)₂-phenyl) | H | C₂H₅ |

TABLE 1-12

| Compound No. | X | R¹ | R² | R³ |
|---|---|---|---|---|
| 98 | S | -CH(phenyl)(2-pyridyl) | H | C₂H₅ |
| 99 | S | -CH(CH₃)(2-pyridyl) | H | C₂H₅ |
| 100 | S | -CH(CH₃)(3-pyridyl) | H | C₂H₅ |
| 101 | S | -(CH₂)₃-N(piperazinyl)-(2-pyridyl) | H | C₂H₅ |
| 102 | S | -(CH₂)₄-N(morpholinyl) | H | C₂H₅ |
| 103 | S | -(CH₂)₃-N(imidazolyl) | H | C₂H₅ |

TABLE 1-13

| Compound No. | X | R¹ | R² | R³ |
|---|---|---|---|---|
| 104 | S | -(CH₂)₃-N(CH₃)₂ | H | C₂H₅ |
| 105 | S | -(CH₂)₂-(1-methylpyrrolidin-2-yl) | H | C₂H₅ |

TABLE 1-13-continued

| Compound No. | X | R¹ | R² | R³ |
|---|---|---|---|---|
| 106 | S | —(CH₂)₃—N(C₂H₅)₂ | H | C₂H₅ |
| 107 | S | —(CH₂)₄—N(piperazine)N—C₆H₄—OCH₃ | H | C₂H₅ |
| 108 | S | —CH₂—(piperidine)N—CH₂—C₆H₅ | H | C₂H₅ |
| 109 | S | —(CH₂)₃—N(piperazine)N—(pyrimidinyl) | H | C₂H₅ |
| 110 | S | —(CH₂)₃—N(thiomorpholine) | H | C₂H₅ |

TABLE 1-14

| Compound No. | X | R¹ | R² | R³ |
|---|---|---|---|---|
| 111 | S | —(CH₂)₃—N(2,6-dimethylmorpholine) | H | C₂H₅ |
| 112 | S | —(CH₂)₄—N(thiomorpholine) | H | C₂H₅ |
| 113 | O | —(CH₂)₅—N(thiomorpholine) | H | C₂H₅ |
| 114 | S | —(CH₂)₅—N(thiomorpholine) | H | C₂H₅ |

TABLE 1-14-continued

| Compound No. | X | R¹ | R² | R³ |
|---|---|---|---|---|
| 115 | S | —(CH₂)₅—N(2,6-dimethylmorpholine) | H | C₂H₅ |

Then, PDE inhibitory activity and pharmacological activity of the representative compounds (I) are described in more detail.

Test Example 1:

The inhibitory activity on PDE derived from canine tracheal smooth muscle (1) Purification of an enzyme According to the method of Torphy [Mol. Pharmacol., 37, 206 (1990)], PDE I (PDE which is activated by calmodulin), PDE II (PDE which is activated by cGMP), PDE III (cAMP-specific PDE which is inhibited by cGMP), PDE IV (cAMP-specific PDE) and PDE V (cGMP-specific PDE) were purified from canine tracheal smooth muscle.

(2) Measurement of PDE activity

The activity was measured based on the method of Kincaid et al. [J. D. Corbin et al., Methods Enzymol., 159, 457 (1988), Academic Press, New York]. The measurement of the PDE I activity was carried out using 1.0 μM [³H] cAMP as a substrate in the presence of 0.4 mM CaCl₂ and 20 units/ml calmodulin. The measurement of the PDE II activity was carried out using 1.0 μM [³H]cAMP as a substrate in the presence of 10 μM cGMP. The measurement of the PDE III, IV and V activity was carried out using, as a substrate, 1.0 μM [³H]cAMP, 1.0 μM [³H]cAMP and 1.0 μM [3H]cGMP, respectively. For measuring the PDE III activity, 10 μM of rolipram which is a PDE IV-selective inhibitor was added to inhibit the PDE IV activity present therein. For measuring the PDE IV activity, 25 μM cGMP was added to inhibit the PDE III activity present therein. Respective reactions were carried out in a buffer having the following composition:

50 mM N,N-bis(2-hydroxyethyl)-2-aminoethanesulfonic acid (pH 7.2), 1 mM MgCl₂, 0.1 mg/ml soybean trypsin inhibitor.

The reaction was started by addition of an enzyme and stopped by addition of hydrochloric acid after 10 to 30 minutes at 30° C. Thereafter, sodium hydroxide was added to neutralize and 5'-AMP or 5'-GMP was converted into adenosine or guanosine using 5'-nucleotidase. The reaction solution was subjected to DEAE-Sephadex A-25 column. [³H]Adenosine [³H]guanosine was eluted with distilled water and the radioactivity was measured with a liquid scintillation counter. The PDE inhibitors were dissolved in 1.7% DMSO.

The results on the PDE inhibitory activity are shown in Table 2.

TABLE 2

| Compound | PDE Inhibitory activity* | | | | |
|---|---|---|---|---|---|
| No. | PDE V | III | IV | I | II |
| 15 | 67%(1 nM) | 50%(1 μM) | | | |
| 20 | 69%(1 nM) | 47%(1 μM) | | | |
| 30 | 0.18 | 1100 | >10000 | 58%(10 μM) | 61%(10 μM) |
| 42 | 94%(1 nM) | 27%(1 μM) | | | |
| 47 | 91%(1 nM) | 60%(1 μM) | 20%(10 μM) | 12%(10 μM) | 19%(10 μM) |
| 51 | 97%(1 nM) | 48%(1 μM) | | | |
| 54 | 96%(1 nM) | 32%(1 μM) | | | |

*Percent inhibition (%) or IC₅₀ value(nM)

Test Example 2:

Hypotensive effects in guinea pigs.

After a guinea pig, anesthetized with pentobarbital, was fixed in the supine position, a cannula was inserted into trachea and guinea pig was artificially ventilated under the conditions of a tidal volume of 10 mg/kg and 60 breathes/min. The carotid artery and the jugular vein were cannulated for measuring arterial blood pressure and administering drugs, respectively. Drugs were dissolved in DMSO (50 μl) and administered intravenously using the above cannula.

The maximum percent values from the pre-drug level (100%) in mean blood pressure (mBP) were obtained. The results thereof are shown in Table 3.

TABLE 3

| Hypotensive activity (guinea pigs, i.v.) | | | | |
|---|---|---|---|---|
| Dose of drug (μg/kg) | 1 | 3 | 10 | 30 |
| DMSO only | | | | |
| mBP(%) | 113.40 | 115.30 | 107.30 | 101.70 |
| ± SEM | 4.10 | 5.20 | 4.70 | 3.60 |
| Compound 39 and DMSO | | | | |
| mBP(%) | 100.20 | 80.00 | 72.30 | 51.20 |
| ± SEM | 5.10 | 6.80 | 7.70 | 5.70 |

Compound (I) or pharmacologically acceptable salts thereof can be formulated into the normally employed forms, for example, tablets, capsules, injections, drops, suppositories and the like and the resulting preparations can be administered orally or parenterally, for example, intramuscularly, intravenously, intra-arterialy, by instillation, or rectally by suppositories. Formulation into those oral or parenteral preparations normally uses the known methods. Preparations may contain various excipients, lubricant, binding agent, disintegrating agent, suspending agent, isotonicity, emulsifying agent and the like.

The examples of carriers to be used for preparations are water, distilled water for injection, physiological saline, glucose, sucrose, mannitol, lactose, starch, cellulose, methylcellulose, carboxymethyl cellulose, hydroxypropyl cellulose, alginate, talc, sodium citrate, calcium carbonate, calcium hydrogenphosphate, magnesium stearate, urea, silicone resin, sorbitan fatty acid ester, glyceric acid ester and the like.

Dose and frequency of administration are varied depending upon dosage form, and age, weight and conditions of patients. Normally, the oral dose of 0.05–5 g/60 kg/day is suitable. In the case of instillation, the dose is preferably in a range of 0.01–5 mg/kg/min. and does not exceed the limit of the oral dose per day.

BEST MODE FOR PRACTISING THE INVENTION

The following Examples and Reference Examples illustrate the aspects of the present invention.

The measurement of proton nuclear magnetic resonance spectrum (NMR) in Examples and Reference Examples was carried out at 270 MHz unless otherwise indicated. Peak positions are expressed as units of 1/million (ppm) downfield from tetramethylsilane. Peak shapes are expressed as follows: s:singlet, d:doublet, t:triplet, q:quartet, m:multiplet, br:broad

Reference Example 1

4-benzylamino-7-chloro-6-nitroquinazoline

7-Chloro-6-nitro-4(3H)-quinazolone [J. Org. Chem., 40, 356 (1975) etc.] (10 g, 54.8 mmol) was added to phosphorus oxychloride (40 ml) under ice-cooling. A temperature of the mixture was gradually raised and the mixture was refluxed for 2 hours. After evaporation of the solvent under reduced pressure, a solution of triethylamine (200 ml, 1.43 mol) and benzylamine (40 ml, 366 mmol) dissolved in tetrahydrofuran (500 ml) was added to the residue under ice-cooling. A temperature of the mixture was raised to room temperature and the mixture was stirred overnight. After evaporation of the solvent under reduced pressure, water and chloroform were added and the organic layer was separated. The aqueous layer was extracted with chloroform and the chloroform layer was combined with the organic layer. The combined organic layer was washed with water and dried over anhydrous magnesium sulfate. After evaporation of the solvent under reduced pressure, a mixed solvent of methanol and water was added thereto. The precipitated crystals were filtered off to give the title compound (8.55 g, 49.6%).

$^1$H-NMR(DMSO-$d_6$+CDCl$_3$, 90 MHz) δ(ppm): 4.84(2H, d, J=5.5 Hz), 7.2–7.5(5H, m), 7.87(1H, s), 8.63(1H, s), 8.9–9.2(1H, br), 9.23(1H, s).

Reference Example 2

4-benzylamino-7-methylamino-6-nitroquinazoline

4-Benzylamino-7-chloro-6-nitroquinazoline (4.3 g, 13.7 mmol) obtained in Reference Example 1 was suspended in a mixed solution of 40% aqueous methylamine solution (35 ml) and ethanol (65 ml) and the suspension was reacted at 110° C. for 4 hours and 40 minutes in a sealed tube. After cooling to room temperature, the reaction mixture was poured into water and the precipitated crystals were filtered off to give the title compound (3.84 g, 90.5%).

hu 1H-NMR(DMSO-$d_6$, 90 MHz) δ(ppm): 2.95(3H, d, J=6 Hz), 4.73(2H, d, J=6 Hz), 6.79(1H, s), 7.2–7.4(5H, m), 7.7–8.0(1H, m), 8.33(1H, s), 9.1–9.3(1H, m), 9.30(1H, s).

Reference Example 3

4-benzylamino-7-ethylamino-6-nitroquinazoline

According to the same manner as that in Reference Example 2 except that a 70% aqueous ethylamine solution was used in place of a 40% aqueous methylamine solution, the title compound (yield 61.3%) was obtained. $^1$H-NMR(DMSO-$d_6$+CDCl$_3$, 90 MHz) δ(ppm): 1.40(3H, t, J=7.1 Hz), 3.2–3.6(2H, m), 4.83(2H, d, J=5.5 Hz), 6.91(1H, s), 7.2–7.5 (5H, m), 7.5–7.8(1H, br), 8.42(1H, s), 8.90(1H, br), 9.33 (1H, s).

Reference Example 4

4-benzylamino-7-isopropylamino-6-nitroquinazoline

A mixture of 4-benzylamino-7-chloro-6-nitroquinazoline (2.1 g, 6.7 mmol) obtained in Reference Example 1 and isopropylamine (18 ml, 438.8 mmol) was heated with stirring at 120° C. for 4 hours in a sealed tube. After evaporation of the solvent under reduced pressure, a mixed solvent of water and ethanol was added to the residue and the precipitated crude crystals were filtered off. The crystals were purified by silica gel column chromatography (gradient elution of ethyl acetate:hexane=5:1–1:1) to give the crystals of the title compound (805.2 mg, 35.8%).

$^1$H-NMR(CDCl$_3$, 90 MHz) δ(ppm): 1.35(6H, d, J=6.37 Hz), 3.84(1H, m), 4.85(2H, d, J=5.5 Hz), 6.35(1H, m), 7.01(1H, s), 7.34–7.44(5H, m), 7.68(1H, m), 8.53(1H, s), 8.73(1H, s).

Reference Example 5

4-benzylamino-6-nitro-7-(n-propylamino) quinazoline (Compound A) and 6-nitro-4,7-bis(n-propylamino)quinazoline (Compound B)

A mixture of 4-benzylamino-7-chloro-6-nitroquinazoline (2.3 g, 7.3 mmol) obtained in Reference Example 1, n-propylamine (10 ml, 235 mmol) and ethanol (10 ml) was heated with stirring at 120 ° C. for 5 hours in a sealed tube. Water was added to the reaction solution and the mixture was extracted with chloroform. The extract was washed with water, dried and evaporated under reduced pressure. The residue was purified by silica gel column chromatography (gradient elution of chloroform-chloroform:methanol=25:1) to give the crystals of Compound A (300 mg, 12%) and crystals of Compound B (910 mg, 43%).

Compound A $^1$H-NMR(CDCl$_3$) δ(ppm): 1.07(3H, t, J=7.4 Hz), 1.80 (2H, m), 3.42(2H, dt, J=6.9, 11.4 Hz), 4.88(2H, d, J=5.4 Hz), 6.50(1H, m), 7.08(1H, s), 7.29–7.41(5H, m), 7.83(1H, m), 8.54(1H, s), 8.77(1H, s).

Compound B $^1$H-NMR(DMSO-$d_6$) δ(ppm): 0.94(6H, t, J=7.4 Hz), 1.66 (4H, m), 3.33(2H, m), 3.46(2H, m), 6.83(1H, s), 7.80(1H, t, J=5.4 Hz), 8.31(1H, s), 8.71(1H, t, J=5.4 Hz), 9.23(1H, s).

The following compounds of Reference Examples 6 to 11 were prepared according to a manner similar to that in Reference Example 4 except for using the corresponding amines in place of isopropylamine.

Reference Example 6

4-benzylamino-7-(n-butylamino)-6-nitroquinazoline $^1$H-NMR(CDCl$_3$) δ(ppm): 0.99(3H, t, J=7.4 Hz), 1.50 (2H, m), 1.75(2H, m), 3.32(2H, dt, J=6.9, 11.4 Hz), 4.86(2H, d, J=4.9 Hz), 6.46(1H, m), 7.01(1H, s), 7.30–7.42(5H, m), 7.77(1H, m), 8.53(1H, s), 8.74(1H, s).

Reference Example 7

4-benzylamino-7-cyclopentylamino-6-nitroquinazoline $^1$H-NMR(DMSO-$d_6$, 90 MHz) δ(ppm): 1.5–2.3(8H, m), 3.9–4.2(1H, m), 4.75(2H, d, J=5.7 Hz), 6.91(1H, s), 7.2–7.4 (5H, m), 7.61(1H, br d, J=5.9 Hz), 8.33 (1H, s), 9.1–9.3(1H, br), 9.29(1H, s).

Reference Example 8

4-benzylamino-7-cyclohexylamino-6-nitroquinazoline $^1$H-NMR(DMSO-$d_6$, 90 MHz) δ(ppm): 1.2–2.2(10H, m), 3.5–3.9(1H, m), 4.73(2H, d, J=5 Hz), 6.91(1H, s), 7.2–7.5 (5H, m), 7.57(1H, d, J=7 Hz), 8.31(1H, s), 9.2–9.4(1H, m), 9.39(1H, s).

Reference Example 9

4-benzylamino-7-cycloheptylamino-6-nitroquinazoline $^1$H-NMR(CDCl$_3$) δ(ppm): 1.54–2.08(12H, m), 3.63(1H, m), 4.85(2H, d, J=4.0 Hz), 6.89(1H, m), 6.98(1H, m), 7.25–7.40(5H, m), 7.80(1H, m), 8.50(1H, s), 8.83(1H, s).

Reference Example 10

4-benzylamino-7-cyclooctylamino-6-nitroquinazoline $^1$H-NMR(DMSO-$d_6$, 90 MHz) δ(ppm): 1.43–1.92(14H, m), 3.6–4.0(1H, m), 4.75(2H, d, J=5.7 Hz), 6.81(1H, s), 7.2–7.4(5H, m), 7.5–7.7(1H, m), 8.32(1H, s), 9.1–9.3(1H, m), 9.29(1H, s).

Reference Example 11

4,7-bis(benzylamino)-6-nitroquinazoline $^1$H-NMR(DMSO-$d_6$, 90 MHz) δ(ppm): 4.69(2H, d, J=5.9 Hz), 5.10(2H, s), 6.83(1H, s), 7.25–7.45(10H, m), 8.46(1H, s), 8.75–8.85(1H, m), 8.82(1H, s).

Reference Example 12

7-ethylamino-6-nitro-4(3H)-quinazolone

A 70% aqueous ethylamine solution (40 ml) was added to a solution (70 ml) of 7-chloro-6-nitro-4(3H)-quinazolone (6.31 g, 28.4 mmol) in ethanol and the mixture was heated with stirring at 110° C. for 4 hours in a sealed tube. After cooling to room temperature, the reaction mixture was poured into water and the precipitated crystals were filtered off. The crystals were washed with ethanol and dried to give the title compound (2.6 g, 39%).

$^1$H-NMR(DMSO-$d_6$) δ(ppm): 1.26(3H, t, J=6.9 Hz), 3.35–3.50(2H, m), 6.92(1H, s), 8.07(1H, s), 8.10–8.15(1H, m), 8.74(1H, s), 11.9–12.2(1H, br).

Reference Example 13

4-chloro-7-ethylamino-6-nitroquinazolone

7-Ethylamino-6-nitro-4(3H)-quinazoline (2.05 g, 8.76 mmol) obtained in Reference Example 12 was added to phosphorus oxychloride (20 ml) and the mixture was stirred at 120° C. for 2 hours. After a solvent was distilled off, the residue was subjected to azeotrope with toluene and used in the subsequent reaction without purification.

Reference Example 14

7-ethylamino-6-nitro-4-(4-pyridylmethylamino)quinazoline

Triethylamine (10 ml, 72.1 mmol) and 4-picolylamine (4 ml, 39.4 mmol) were added to a tetrahydrofuran solution (20 ml) of 4-chloro-7-ethylamino-6-nitroquinazoline obtained from 7-ethylamino-6-nitro-4(3H)-quinazolone (737.9 mg, 3.15 mmol) according to the procedures in Reference Example 13 under ice-cooling. The mixture was stirred at room temperature for 13 hours and at 55° C. for 4 hours. After a solvent was distilled off, the residue was purified by silica gel column chromatography (eluted with ethyl acetate:hexane=9:1) to give the title compound (780 mg, 76%).

$^1$H-NMR(CDCl$_3$) δ(ppm): 1.42(3H, t, J=6.9 Hz), 3.41 (2H, m), 4.94(2H, d, J=3.5 Hz), 7.10(1H, s), 7.35(2H, m, J=7.9 Hz), 7.75(2H, d, J=7.9 Hz), 8.01(1H, br), 8.54(1H, s), 8.67(1H, m), 8.90(1H, s).

The following compounds of Reference Examples 15 to 65 were prepared according to a manner similar to that in Reference Example 14 except for using the corresponding amines in place of 4-picolylamine.

Reference Example 15

7-ethylamino-6-nitro-4-(3-pyridylmethylamino)quinazoline $^1$H-NMR(DMSO-$d_6$) δ(ppm): 1.26(3H, t, J=6.9 Hz), 3.37 (2H, m), 4.76(2H, d, J=5.4 Hz), 7.36(1H, m), 7.77(2H, m), 8.32(1H, s), 8.47(1H, dd, J=5.0, 1.5 Hz), 8.60(1H, br), 9.24(1H, m), 9.26(1H, s).

Reference Example 16

7-ethylamino-6-nitro-4-(2-pyridylmethylamino)quinazoline $^1$H-NMR(DMSO-$d_6$) δ(ppm): 1.27(3H, t, J=7.3 Hz), 3.39 (2H, m), 4.83(2H, d, J=5.6 Hz), 6.89(2H, d, J=5.6 Hz), 7.27(1H, dd, J=7.3, 5.0 Hz), 7.33(1H, d, J=7.9 Hz), 7.74(2H, m), 8.30(1H, s), 8.52(1H, d, J=4.6 Hz), 9.33(1H, s), 9.35 (1H, br).

Reference Example 17

7-ethylamino-4-(4-methoxybenzylamino)-6-nitroquinazoline $^1$H-NMR(CDCl$_3$) δ(ppm): 1.40(3H, t, J=7.2 Hz), 3.37 (2H, dq, J=7.2, 5.0 Hz), 3.81(3H, s), 4.78(2H, d, J=5.3 Hz), 6.2–6.3(1H, m), 6.90(2H, d, J=8.5 Hz), 7.00(1H, s), 7.33 (2H, d, J=8.5 Hz), 8.55(1H, s), 8.71(1H, s).

Reference Example 18

7-ethylamino-4-(3-methoxybenzylamino)-6-nitroquinazoline $^1$H-NMR(CDCl$_3$) δ(ppm): 1.40(3H, t, J=7.3 Hz), 3.37 (2H, dq, J=7.3, 4.9 Hz), 3.80(3H, s), 4.83(2H, d, J=5.2 Hz), 6.2–6.3(1H, m), 6.86(1H, dd, J=8.2, 2.4 Hz), 6.9–7.0(3H, m), 7.25–7.35(1H, m), 7.6–7.7(1H, m), 8.55(1H, s), 8.72 (1H, s).

Reference Example 19

7-ethylamino-4-(2-methoxybenzylamino)-6-nitroquinazoline $^1$H-NMR(CDCl$_3$) δ(ppm): 1.40(3H, t, J=7.1 Hz), 3.37 (2H, dq, J=7.3, 5.0 Hz), 3.93(3H, s), 4.86(2H, d, J=5.6 Hz), 6.45–6.55(1H, m), 6.85–7.0(3H, m), 7.25–7.40(2H, m), 7.65–7.75(1H, m), 8.53(1H, s), 8.67(1H, s).

Reference Example 20

7-ethylamino-4-(4-methylbenzylamino)-6-nitroquinazoline $^1$H-NMR(CDCl$_3$) δ(ppm): 1.41(3H, t, J=7.1 Hz), 2.33 (3H, s), 3.39(2H, q, J=7.1 Hz), 4.77(2H, s), 6.90(1H, s), 7.14(2H, d, J=7.9 Hz), 7.28(2H, d, J=7.9 Hz), 7.54(1H, s), 8.41(1H, s), 9.30(1H,s).

Reference Example 21

7-ethylamino-6-nitro-4-(3-trifluoromethylbenzylamino)quinazoline $^1$H-NMR(CDCl$_3$) δ(ppm): 1.41(3H, t, J=7.1 Hz), 3.35–3.45(2H, m), 4.89(2H, d, J=5.3 Hz), 6.98(1H, s), 7.4–7.8(5H, m), 8.46(1H, s), 8.85–8.95(1H, m), 9.30(1H, s).

Reference Example 22

7-ethylamino-4-(4-fluorobenzylamino)-6-nitroquinazoline $^1$H-NMR(CDCl$_3$) δ(ppm): 1.40(3H, t, J=7.2 Hz), 3.39 (2H, m), 4.85(2H, d, J=5.3 Hz), 7.0–7.1(3H, m), 7.35–7.45 (2H, m), 7.65–7.8(1H, m), 8.53(1H, s), 8.87(1H, s).

Reference Example 23

4-(3,4-difluorobenzylamino)-7-ethylamino-6-nitroquinazoline $^1$H-NMR(CDCl$_3$) δ(ppm): 1.41(3H, t, J=7.2 Hz), 3.3–3.5 (2H, m), 4.84(2H, d, J=5.6 Hz), 6.2–6.4(1H, br), 7.02(1H, s), 7.1–7.3(3H, m), 7.65–7.75(1H, br), 8.54(1H, s), 8.76(1H, s).

Reference Example 24

4-(4-chlorobenzylamino)-7-ethylamino-6-nitroquinazoline $^1$H-NMR(CDCl$_3$) δ(ppm): 1.41(3H, t, J=7.1 Hz), 3.3–3.45(2H, m), 4.79(2H, d, J=5.6 Hz), 6.94(1H, s), 7.25–7.4(4H, m), 7.6–7.7(1H, m), 8.47(1H, s), 9.23(1H, s).

Reference Example 25

4-(N-benzyl-N-methylamino)-7-ethylamino-6-nitroquinazoline $^1$H-NMR(CDCl$_3$) δ(ppm): 1.40(3H, t, J=7.3 Hz), 3.3–3.45(2H, m), 3.42(3H, s), 5.06(2H, s), 6.99(1H, s), 7.2–7.5(5H, m), 7.55–7.65(1H, m), 8.51(1H, s), 9.00(1H, s).

Reference Example 26

4-amino-7-ethylamino-6-nitroquinazoline $^1$H-NMR(DMSO-d$_6$) δ(ppm): 1.27(3H, t, J=7.0 Hz), 3.3–3.45(2H, m), 6.83(1H, s), 7.65–7.75(1H, m), 8.25(1H, s), 9.20(1H, s).

Reference Example 27

4,7-bis(ethylamino)-6-nitroquinazoline $^1$H-NMR(DMSO-d$_6$) δ(ppm): 1.24(6H, t, J=7.3 Hz), 3.37 (2H, m), 3.53(2H, m), 6.83(1H, s), 7.72(1H, t, J=5.3 Hz), 8.32(1H, s), 8.68(1H, br), 9.20(1H, s).

Reference Example 28

7-ethylamino-4-(indan-1-ylamino)-6-nitroquinazoline $^1$H-NMR(CDCl$_3$) δ(ppm): 1.41(3H, t, J=7.1 Hz), 2.0–2.15(1H, m), 2.7–2.85(1H, m), 2.9–3.2(2H, m), 3.3–3.45(2H, m), 6.00(1H, q, J=7.3 Hz), 6.2–6.3(1H, br), 7.06(1H, s), 7.15–7.4(4H, m), 7.65–7.75(1H, m), 8.56(1H, s), 8.69 (1H, s).

Reference Example 29

7-ethylamino-6-nitro-4-phenylaminoquinazoline $^1$H-NMR(DMSO-d$_6$) δ(ppm): 1.28(3H, t, J=7.3 Hz), 3.41 (2H, dq, J=5.6, 7.3 Hz), 6.94(1H, s), 7.15(1H, m), 7.39(2H, m), 7.79(3H, m), 8.43(1H, s), 9.51(1H, s), 10.17(1H, br).

Reference Example 30

7-ethylamino-6-nitro-4-(2-phenethylamino)quinazoline $^1$H-NMR(CDCl$_3$+CD$_3$OD) δ(ppm): 1.41(3H, t, J=7.4 Hz), 3.03(2H, t, J=7.4 Hz), 3.39(2H, m), 3.86(2H, t, J=7.4 Hz), 6.93(1H, s), 7.24–7.35(5H, m), 8.43 (1H, s), 8.86(1H, s).

Reference Example 31

7-ethylamino-4-(1-naphthylmethylamino)-6-nitroquinazoline $^1$H-NMR(CDCl$_3$) δ(ppm): 1.39(3H, t, J=7.3 Hz), 3.37 (2H, dt, J=7.3, 5.0 Hz), 5.28(1H, d, J=4.6 Hz), 6.18(1H, br), 7.01(1H, s), 7.51(4H, m), 7.65(1H, m), 7.89(2H, m), 8.04 (1H, m), 8.61(2H, s).

Reference Example 32

4-(diphenylmethylamino)-7-ethylamino-6-nitroquinazoline $^1$H-NMR(CDCl$_3$) δ(ppm): 1.41(3H, t, J=7.1 Hz), 3.3–3.5 (2H, m), 6.29(1H, br d, J=7.3 Hz), 6.77(1H, d, J=7.3 Hz), 7.04(1H, s), 7.2–7.4(10H, m), 7.71(1H, br), 8.49(1H, s), 8.75(1H, s).

Reference Example 33

7-ethylamino-6-nitro-4-(2,3,4,5-tetrahydro-2-furylmethylamino)quinazoline $^1$H-NMR(CDCl$_3$) δ(ppm): 1.39(3H, t, J=6.9 Hz), 1.68 (1H, m), 1.98(2H, m), 2.15(1H, m), 3.34(2H, m), 3.45(1H, m), 3.88(1H, m), 3.99(2H, m), 4.34(2H, dq, J=6.9, 4.5 Hz), 6.72(1H, s), 6.87(1H, s), 6.95(1H, br), 7.27(1H, s), 7.65(1H, t, J=4.5 Hz), 8.39(1H, s), 8.70(1H, s).

Reference Example 34

7-ethylamino-6-nitro-4-(2-thienylmethylamino)quinazoline $^1$H-NMR(DMSO-d$_6$) δ(ppm): 1.16(3H, t, J=7.3 Hz), 4.90 (2H, d, J=5.6 Hz), 6.87(1H, s), 6.97(1H, m), 7.09(1H, d, J=3.0 Hz), 7.38(1H, dd, J=5.0, 1.3 Hz), 7.75(1H, t, J=5.3 Hz), 8.39(1H, s), 9.23(1H, s), 9.30(1H, t, J=5.6 Hz).

Reference Example 35

7-ethylamino-6-nitro-4-(4-phenylpiperazin-1-yl)quinazoline $^1$H-NMR(CDCl$_3$) δ(ppm): 1.42(3H, t, J=7.1 Hz), 3.3–3.5 (6H, m), 4.05–4.15(4H, m), 6.85–7.0(3H, m), 7.06(1H, s), 7.2–7.4(2H, m), 7.65–7.75(1H, m), 8.54(1H, s), 8.92(1H, s).

Reference Example 36

4-(4-benzylpiperazin-1-yl)-7-ethylamino-6-nitroquinazoline $^1$H-NMR(CDCl$_3$) δ(ppm): 1.41(3H, t, J=7.1 Hz), 2.65–2.75(4H, m), 3.35–3.50(2H, m), 3.63(2H, s), 3.95–4.05(4H, m), 7.07(1H, s), 7.3–7.4(5H, m), 7.65–7.75 (1H, m), 8.50(1H, s), 8.85(1H, s).

Reference Example 37

4-(4-benzylpiperidino)-7-ethylamino-6-nitroquinazoline $^1$H-NMR(CDCl$_3$, 90 MHz) δ(ppm): 1.42(3H, t, J=7 Hz), 1.6–2.1(5H, m), 2.4–2.8(3H, m), 3.0–3.3(1H, m), 3.3–3.6 (2H, m), 4.3–4.7(2H, m), 7.04(1H, s), 7.1–7.5(5H, m), 7.5–7.8(1H, m), 8.55(1H, s), 8.92(1H, s).

Reference Example 38

7-ethylamino-6-nitro-4-piperidinoquinazoline $^1$H-NMR(CDCl$_3$, 90 MHz) δ(ppm): 1.42(3H, t, J=7 Hz), 1.7–1.9(6H, m), 3.42(2H, dd, J=7, 5 Hz), 3.7–4.0(4H, m), 7.05(1H, s), 7.5–7.8(1H, br), 8.55(1H, s), 8.93(1H, s).

Reference Example 39

4-[N-(2-dimethylaminoethyl)-N-methylamino]-7-ethylamino-6-nitroquinazoline $^1$H-NMR(CDCl$_3$, 90 MHz) δ(ppm): 1.38(3H, t, J=6.9 Hz), 2.35(6H, s), 2.7–2.9(2H, m), 3.4–3.6(2H, m), 3.49(3H, s), 3.8–4.1(2H, m), 6.96(1H, s), 8.45 (1H, s), 9.17(1H, s).

Reference Example 40

7-ethylamino-4-(4-methylhomopiperazin-1-yl)-6-nitroquinazoline

¹H-NMR(CDCl₃, 90 MHz) δ(ppm): 1.40(3H, t, J=6.9 Hz), 2.1–2.3(2H, m), 2.42 (3H, s), 2.6–2.8(2H, m), 2.8–3.0 (2H, m), 3.3–3.6(2H, m), 4.0–4.2(2H, m), 6.97(1H, s), 8.47(1H, s), 9.04(1H, s).

Reference Example 41

4-(bicyclo[2.2.1]heptan-2-ylamino)-7-ethylamino-6-nitroquinazoline

¹H-NMR(CDCl₃) δ(ppm): 1.2–1.7(7H, m), 1.41(3H, t, J=7.2 Hz), 1.9–2.1(1H, m), 2.42(2H, br), 3.3–3.5(2H, m), 4.1–4.2(1H, m), 5.8–5.9(1H, br), 7.03(1H, s), 7.71(1H, br), 8.51(1H, s), 8.70(1H, s).

Reference Example 42

4-(cyclohexylmethylamino)-7-ethylamino-6-nitroquinazoline

¹H-NMR(DMSO-d₆) δ(ppm): 0.93–1.02(2H, m), 1.15 (3H, m), 1.26(3H, t, J=6.9 Hz), 1.64–1.76(6H, m), 3.34(4H, m), 6.84(1H, s), 7.73(1H, t, J=5.4 Hz), 8.31(1H, s), 8.69(1H, t, J=5.4 Hz), 9.26(1H, s).

Reference Example 43

7-ethylamino-4-(3-morpholinopropylamino)-6-nitroquinazoline

¹H-NMR(CDCl₃) δ(ppm): 1.41(3H, t, J=7.2 Hz), 1.9–2.0 (2H, m), 2.6–2.7(4H, m), 2.7–2.8(2H, m), 3.3–3.5(2H, m), 3.75–3.85(2H, m), 3.9–4.0(4H, m), 6.99(1H, s), 7.7–7.8(1H, br), 8.35–8.45(1H, br), 8.48(1H, s), 8.82(1H, s).

Reference Example 44

7-ethylamino-4-(2-morpholinoethylamino)-6-nitroquinazoline

¹H-NMR(CDCl₃) δ(ppm): 1.41(3H, t, J=7.1 Hz), 2.5–2.6 (4H, m), 2.74(2H, t, J=6.0 Hz), 3.3–3.45(2H, m), 3.7–3.85 (6H, m), 6.7–6.9(1H, m), 6.97(1H, s), 7.6–7.75(1H, m), 8.50(1H, s), 8.76(1H, s).

Reference Example 45

7-ethylamino-6-nitro-4-[2-(3-pyridyl)ethylamino]quinazoline

¹H-NMR(CDCl₃) δ(ppm): 1.41(3H, t, J=7.1 Hz), 3.08 (2H, t, J=7.1 Hz), 3.35–3.45(2H, m), 3.96(2H, q, J=7.0 Hz), 6.6–6.7(1H, m), 7.02(1H, s), 7.2–7.3 (1H, m), 7.55–7.65 (1H, m), 7.65–7.75(1H, m), 8.45–8.5(2H, m), 8.53(1H, s), 8.73(1H, s).

Reference Example 46

7-ethylamino-6-nitro-4-[2-(2-pyridyl)ethylamino]quinazoline

¹H-NMR(CDCl₃) δ(ppm): 1.41(3H, t, J=7.2 Hz), 3.19 (2H, t, J=5.9 Hz), 3.35–3.45(2H, m), 4.0–4.1(2H, m), 7.05 (1H, s), 7.2–7.3(1H, m), 7.65–7.8(2H, m), 8.49(1H, s), 8.7–8.8(1H, m), 8.90(1H, s).

Reference Example 47

7-ethylamino-6-nitro-4-[2-(4-pyridyl)ethylamino]quinazoline

¹H-NMR(CDCl₃) δ(ppm): 1.40(3H, t, J=7.2 Hz), 3.07 (2H, t, J=7.0 Hz), 3.3–3.5(2H, m), 3.97(2H, q, J=6.6 Hz), 6.7–6.8(1H, m), 7.00(1H, s), 7.18(2H, d, J=6.0 Hz), 7.65–7.75(1H, m), 8.48(2H, d, J=6.0 Hz), 8.54(1H, s), 8.72(1H, s).

Reference Example 48

7-ethylamino-6-nitro-4-[2-(1-pyrrolidinyl)ethylamino]quinazoline

¹H-NMR(CDCl₃) δ(ppm): 1.40(3H, t, J=7.2 Hz), 1.75–1.95(4H, m), 2.6–2.8(2H, m), 2.91(2H, t, J=6.0 Hz), 3.3–3.45(2H, m), 3.78(2H, t, J=6.0 Hz), 6.94(1H, s), 7.6–7.8 (2H, m), 8.46(1H, s), 9.01(1H, s).

Reference Example 49

7-ethylamino-6-nitro-4-(2-piperidinoethylamino)quinazoline

¹H-NMR(CDCl₃) δ(ppm): 1.41(3H, t, J=7.2 Hz), 1.45–1.6(2H, m), 1.6–1.7(4H, m), 2.45–2.6(4H, m), 2.67 (2H, t, J=5.9 Hz), 3.3–3.45(2H, m), 3.66(2H, t, J=5.6 Hz), 6.97(1H, s), 7.0–7.2(1H, br), 7.65–7.75(1H, m), 8.49(1H, s), 8.78(1H, s).

Reference Example 50

7-ethylamino-4-(4-dimethylaminobenzylamino)-6-nitroquinazoline

¹H-NMR(CDCl₃+CD₃OD) δ(ppm): 1.41(3H, t, J=7.3 Hz), 2.95(6H, s), 3.42(2H, q, J=7.3 Hz), 4.70(2H, s), 6.74 (2H, d, J=8.9 Hz), 6.93(1H, s), 7.29(2H, d, J=8.9 Hz), 7.34(1H, s), 7.70–7.78(1H, br), 8.44(1H, s), 8.91(1H, s).

Reference Example 51

7-ethylamino-6-nitro-4-[α-(2-pyridyl)benzylamino]quinazoline

¹H-NMR(CDCl₃) δ(ppm): 1.40(3H, t, J=7.3 Hz), 3.32–3.41(2H, m), 6.60(1H, d, J=6.3 Hz), 6.96(1H, s), 7.21–7.40(4H, m), 7.40–7.48(2H, m), 7.62–7.72 (2H, m), 8.45(1H, s), 8.52–8.57(1H, m), 8.64(1H, d, J=4.6 Hz), 8.97 (1H, s).

Reference Example 52

7-ethylamino-6-nitro-4-[1-(2-pyridyl)ethylamino]quinazoline

¹H-NMR(CDCl₃) δ(ppm): 1.41(3H, t, J=7.1 Hz), 1.65 (3H, d, J=6.6 Hz), 3.39 (2H, m), 5.55–5.60(1H, m), 7.01(1H, s), 7.26–7.36(1H, m), 7.70–7.76(2H, m), 7.90–8.00(1H, br), 8.51(1H, s), 8.66(1H, d, J=4.6 Hz), 8.86(1H, s).

Reference Example 53

7-ethylamino-6-nitro-4-[1-(3-pyridyl)ethylamino]quinazoline

¹H-NMR(CDCl₃) δ(ppm): 1.39(3H, t, J=7.3 Hz), 1.74 (3H, d, J=6.9 Hz), 3.35 (2H, q, J=7.3 Hz), 5.66–5.72(1H, m), 6.71(1H, d, J=7.3 Hz), 6.97(1H, s), 7.26–7.30(1H, m), 7.63–7.71(1H, m), 7.77(1H, d, J=7.3 Hz), 8.47(1H, s), 8.51(1H, d, J=4.6 Hz), 8.71(1H, s), 8.86(1H, s).

Reference Example 54

7-ethylamino-6-nitro-4-{3-[4-(2-pyridyl)piperazinyl]propylamino}quinazoline

¹H-NMR(CDCl₃) δ(ppm): 1.38(3H, t, J=7.1 Hz), 1.95 (2H, m), 2.69–2.74(6H, m), 3.34(2H, q, J=7.1 Hz), 3.67–3.74(6H, m), 6.62–6.71(2H, m), 6.94(1H, s), 7.51(1H, dd, J=1.3, 7.3 Hz), 7.63(1H, br), 8.18–8.21(1H, m), 8.49(1H, s), 8.50(1H, d, J=5.0 Hz), 8.77(1H, s).

Reference Example 55

7-ethylamino-4-(4-morpholinobutylamino)-6-nitroquinazoline $^1$H-NMR(CDCl$_3$+CD$_3$OD) δ(ppm): 1.41(3H, t, J=7.3 Hz), 1.64–1.85(4H, m), 2.46–2.60(6H, m), 3.51(2H, q, J=7.3 Hz), 3.63(2H, t, J=6.4 Hz), 3.72–3.80(4H, m), 6.91(1H, s), 7.32(1H, s), 8.40(1H, s), 9.01(1H, s).

Reference Example 56

7-ethylamino-4-[2-(2-methylpiperidino)ethylamino]-6-nitroquinazoline $^1$H-NMR(CDCl$_3$) δ(ppm): 1.35–1.45(9H, m), 1.90–2.10(2H, m), 2.20–2.35(3H, m), 3.30–3.45(2H, m), 3.75–3.87(2H, m), 6.90(1H, s), 7.60–7.67(1H, m), 8.40(1H, s), 9.40(1H, s).

Reference Example 57

7-ethylamino-4-(3-dimethylaminopropylamino)-6-nitroquinazoline $^1$H-NMR(CDCl$_3$) δ(ppm): 1.36–1.42(3H, m), 1.81–1.92(2H, m), 2.45(3H, s), 2.46(3H, s), 2.62–2.70(2H, m), 3.33–3.38(2H, m), 3.67–3.73(2H, m), 6.87(1H, s), 7.60–7.70(1H, m), 8.43(1H, s), 8.62(1H, s), 9.90(1H, br).

Reference Example 58

7-ethylamino-4-[2-(1-methyl-2-pyrrolidinyl)ethylamino]-6-nitroquinazoline $^1$H-NMR(CDCl$_3$) δ(ppm): 1.40(3H, t, J=7.2 Hz), 1.80–2.20(8H, m), 2.59(3H, s), 3.33–3.43(3H, m), 3.50–3.95(2H, m), 6.92(1H, s), 7.62–7.70(1H, br), 8.45(1H, s), 8.73(1H, s).

Reference Example 59

7-ethylamino-4-(3-diethylaminopropylamino)-6-nitroquinazoline $^1$H-NMR(CDCl$_3$) δ(ppm): 1.14–1.42(9H, m), 1.85–2.10(2H, m), 2.60–3.00(6H, m), 3.20–3.40(2H, m), 3.55–3.80(2H, m), 6.90(1H, s), 7.64(1H, s), 8.43(1H, s), 8.89(1H, s), 9.51(1H, br).

Reference Example 60

7-ethylamino-4-{4-[4-(4-methoxyphenyl)piperazinyl]butylamino}-6-nitroquinazoline $^1$H-NMR(CDCl$_3$) δ(ppm): 1.41(3H, t, J=7.2 Hz), 1.72–1.87(4H, m), 2.55(2H, t, J=6.9 Hz), 2.69–2.73(4H, m), 3.13–3.16(4H, m), 3.38(2H, q, J=7.2 Hz), 3.67–3.74(2H, m), 3.76(3H, s), 6.55–6.65(1H, m), 6.83(2H, d, J=9.4 Hz), 6.90(2H, d, J=9.4 Hz), 6.98(1H, s), 7.65–7.72(1H, m), 8.50(1H, s), 8.77(1H, s).

Reference Example 61

4-[(1-benzyl-4-piperidinyl)methylamino]-7-ethylamino-6-nitroquinazoline $^1$H-NMR(CDCl$_3$+CD$_3$OD) δ(ppm): 1.40(3H, t, J=7.3 Hz), 1.60–1.80(2H, m), 1.85–2.10(3H, m), 2.35–2.50(2H, m), 3.38(2H, q, J=7.3 Hz), 3.53–3.56(2H, br), 3.86(2H, s), 6.91(1H, d, J=3.0 Hz), 7.33–7.50(5H, m), 7.67(1H, m), 8.37(1H, s), 9.11(1H, s).

Reference Example 62

7-ethylamino-6-nitro-4-{3-[4-(2-pyrimidyl)piperazinyl]propylamino}quinazoline $^1$H-NMR(CDCl$_3$) δ(ppm): 1.39(3H, t, J=7.1 Hz), 1.94–2.01(2H, m), 2.60–2.80(6H, m), 3.38(2H, q, J=7.1 Hz), 3.73–3.80(2H, m), 3.90–4.00(4H, m), 6.50–6.54(1H, m), 7.38(1H, s), 7.67(1H, br), 8.31(1H, s), 8.32(1H, s), 8.45(1H, s), 8.59(1H, br), 9.00(1H, s).

Reference Example 63

7-ethylamino-6-nitro-4-(3-thiomorpholinopropylamino)quinazoline $^1$H-NMR(CDCl$_3$+CD$_3$OD) δ(ppm): 1.42(3H, t, J=7.3 Hz), 1.92(2H, t, J=6.6 Hz), 2.59(2H, t, J=6.6 Hz), 2.77–2.84(8H, m), 3.40(2H, q, J=7.3 Hz), 3.66(2H, t, J=6.6 Hz), 6.91(1H, s), 7.40(1H, s), 8.37(1H, s), 8.95(1H, s).

Reference Example 64

7-ethylamino-4-[3-(2,6-dimethylmorpholino)propylamino]-6-nitroquinazoline (cis and trans mixture)

$^1$H-NMR(CDCl$_3$) δ(ppm): 1.20(3.7H, d, J=6.3 Hz), 1.27(2.3H, d, J=6.6 Hz), 1.41(3H, t, J=6.8 Hz), 1.76–1.98(3H, m), 2.20–2.80(3H, m), 2.80–2.95(2H, m), 3.35–3.45(2H, m), 3.60–3.80(2H, m), 3.80–4.15(2H, m), 6.93(1H, s), 7.31(1H, s), 7.71–7.73(1H, m), 8.41(1H, s), 8.83(1H, s).

Reference Example 65

7-ethylamino-6-nitro-4-(4-thiomorpholinobutylamino)quinazoline $^1$H-NMR(CDCl$_3$+CD$_3$OD) δ(ppm): 1.41(3H, t, J=7.1 Hz), 1.60–1.80(4H, m), 2.46(2H, t, J=7.3 Hz), 2.65–2.80(8H, m), 3.38(2H, q, J=7.1 Hz), 3.63(2H, t, J=6.6 Hz), 6.92(1H, s), 7.30(1H, s), 8.41(1H, s), 8.96(1H, s).

Reference Example 66

4-(5-chloropentylamino)-7-ethylamino-6-nitroquinazoline

Triethylamine (14.9 ml, 106.9 mmol) and 5-amino-1-pentanol (2.47 ml, 22.7 mmol) were added to a 1,4-dioxane solution (100 ml) of 4-chloro-7-ethylamino-6-nitroquinazoline (5.74 g, 22.7 mmol) obtained in Reference Example 13 under ice-cooling and the mixture was stirred at room temperature for 19 hours. The precipitated solid was filtered off, washed successively with water and ether and dried. To a solution of the resulting solid in 1,2-dichloroethane (40 ml), thionyl chloride (4.80 ml, 65.8 mmol) was added and the mixture was heated under reflux for 3 hours. After the solvent was distilled off, ice and a saturated aqueous solution of sodium bicarbonate were added and the mixture was extracted with chloroform. The organic layer was dried over a drying agent (magnesium sulfate), the drying agent was filtered off and the filtrate was concentrated under reduced pressure to give 7.15 g (93.3%) of the title compound as a crude product.

$^1$H-NMR(CDCl$_3$) δ(ppm): 1.40(3H, t, J=7.2 Hz), 1.56–1.65(2H, m), 1.73–1.90(4H, m), 3.39(2H, q, J=7.2 Hz), 3.57(2H, t, J=6.4 Hz), 3.67–3.74(2H, m), 6.43(1H, br), 7.02(1H, s), 7.71–7.74(1H, m), 8.51(1H, s), 8.82(1H, s).

Reference Example 67

7-ethylamino-6-nitro-4-(5-thiomorpholinopentylamino)quinazoline

Thiomorpholine (6 ml, 59.7 mmol) was added to a dimethylformamide solution (30 ml) of 4-(5-chloropentylamino)-7-ethylamino-6-nitroquinazoline (2.50 g, 7.41 mmol) obtained in Reference Example 66 and the mixture was heated under reflux for 3 hours. After the solvent was distilled off, the residue was purified by silica gel column chromatography (chloroform:methanol=30:1) to give the title compound (2.95 g, 98.7%).

$^1$H-NMR(CDCl$_3$) δ(ppm): 1.40(3H, t, J=7.2 Hz), 1.42–1.50(2H, m), 1.59–1.83(4H, m), 2.53(2H, t, J=7.4 Hz), 2.75–2.81(4H, m), 3.32–3.39(6H, m), 3.66(2H, t, J=7.2 Hz), 6.92(1H, s), 7.64–7.67(1H, m), 8.47(1H, s), 8.89(1H, s).

Reference Example 68

7-ethylamino-4-[5-(2,6-dimethylmorpholino)pentylamino]-6-nitroquinazoline

According to a manner similar to that in Reference Example 67, the title compound was obtained from a compound obtained in Reference Example 66 and 2,6-dimethylmorpholine.

$^1$H-NMR(CDCl$_3$) δ(ppm): 1.16–1.30(6H, m), 1.40(3H, t, J=7.2 Hz), 1.42–1.80(6H, m), 2.43(2H, t, J=7.4 Hz), 2.80–2.85(2H, m), 3.30–3.45(4H, m), 3.60–4.05(4H, m), 6.44(1H, br), 6.96(1H, s), 7.66–7.70(1H, m), 8.49(1H, s), 8.84(1H, s).

EXAMPLE 1

8-benzylamino-3-ethyl-2,3-dihydro-1H-imidazo[4,5-g]quinazoline-2-one (Compound 1)

To a solution of 4-benzylamino-7-ethylamino-6-nitroquinazoline (3.00 g, 9.29 mmol) obtained in Reference Example 3 in dimethylformamide (100 ml), was added a suspension of 10% palladium on carbon (300 mg) in water (10 ml), followed by stirring under hydrogen stream at room temperature for 5 hours and additionally at 50° C. for 1 hour. The reaction mixture was filtered with a filter aid and the filtrate was evaporated. The residue was crystallized from methanol to give crude crystals (2.59 g, 95.2%) of 6-amino-4-benzylamino-7-ethylaminoquinazoline. To a solution of the resulting crude crystals (200 mg, 0.683 mmol) in -dimethylformamide (10 ml), was added N,N'-carbonyldiimidazole (300 mg, 1.85 mmol), followed by stirring at 100° C. for 3.5 hours. Water was added to the reaction mixture, the precipitated crystals were filtered off and recrystallized from a mixed solvent of ethanol and dioxane to give the title compound (160 mg, 47.3%).

$^1$H-NMR(DMSO-d$_6$, 90 MHz) δ(ppm): 1.25(3H, t, J=7.0 Hz), 3.92(2H, br q, J=7.0 Hz), 4.78(2H, d, J=5.5 Hz), 7.1–7.5(6H, m), 7.82(1H, s), 8.34(1H, s), 8.45–8.65(1H, m), 11.3–11.4(1H, br).

The following compounds of Examples 2 to 38, Examples 76 to 89 and Example 113 were prepared according to a manner similar to that in Example 1 except for using the corresponding nitro compounds obtained in References in place of 4-benzylamino-7-ethylamino-6-nitroquinazoline.

EXAMPLE 2

8-benzylamino-3-methyl-2,3-dihydro-1H-imidazo[4,5-g]quinazoline-2-one (Compound 2)

This compound was synthesized from the compound obtained in Reference Example 2.

$^1$H-NMR(DMSO-d$_6$, 90 MHz) δ(ppm): 3.37(3H, s), 4.77(2H, d, J=4.6 Hz), 7.2–7.4(5H, m), 7.81(1H, s), 8.32(1H, s), 8.5–8.6(1H, m), 11.38(1H, s).

EXAMPLE 3

8-benzylamino-3-isopropyl-2,3-dihydro-1H-imidazo[4,5-g]quinazoline-2-one (Compound 3)

This compound was synthesized from the compound obtained in Reference Example 4.

$^1$H-NMR(DMSO-d$_6$) δ(ppm): 1.59(6H, d, J=6.9 Hz), 4.72(2H, m), 4.86(2H, s), 7.24–7.41(5H, m), 7.46(1H, s), 7.55(1H, s), 8.47(1H, s).

EXAMPLE 4

8-benzylamino-3-(n-propyl)-2,3-dihydro-1H-imidazo[4,5-g]quinazoline-2-one (Compound 4)

This compound was synthesized from Compound A obtained in Reference Example 5

$^1$H-NMR(DMSO-d$_6$) δ(ppm): 0.90(3H, t, J=7.4 Hz), 1.71(2H, tq, J=6.9, 7.4 Hz), 3.85(2H, t, J=6.9 Hz), 4.77(2H, d, J=5.4 Hz), 7.19–7.36(6H, m), 7.83(1H, s), 8.33(1H, s), 8.60(1H, m), 11.42(1H, s).

EXAMPLE 5

8-benzylamino-3-(n-butyl)-2,3-dihydro-1H-imidazo[4,5-g]quinazoline-2-one (Compound 5)

This compound was synthesized from the compound obtained in Reference Example 6.

$^1$H-NMR(DMSO-d$_6$) δ(ppm): 0.91(3H, t, J=7.4 Hz), 1.32(2H, m), 1.70(2H, m, J=6.9, 7.4 Hz), 3.88(2H, t, J=6.9 Hz), 4.78(2H, d, J=5.4 Hz), 7.19–7.36(6H, m), 7.83(1H, s), 8.32(1H, s), 8.59(1H, t, J=5.9 Hz), 11.42(1H, s).

EXAMPLE 6

8-benzylamino-3-cyclopentyl-2,3-dihydro-1H-imidazo[4,5-g]quinazoline-2-one (Compound 6)

This compound was synthesized from the compound obtained in Reference Example 7.

$^1$H-NMR(DMSO-d$_6$, 90 MHz) δ(ppm): 1.6–2.2(8H, m), 4.65–5.0(3H, m), 7.1–7.4 (6H, m), 7.81(1H, s), 8.31(1H, s), 8.4–8.6(1H, m), 11.4–11.5(1H, br).

EXAMPLE 7

8-benzylamino-3-cyclohexyl-2,3-dihydro-1H-imidazo[4,5-g]quinazoline-2-one (Compound 7)

This compound was synthesized from the compound obtained in Reference Example 8.

$^1$H-NMR(DMSO-d$_6$, 90 MHz) δ(ppm): 1.4–2.0(10H, m), 4.1–4.3(1H, m), 4.65–4.85(2H, m), 7.15–7.40(5H, m), 7.44(1H, s), 7.79(1H, s), 8.31(1H, s).

EXAMPLE 8

8-benzylamino-3-cycloheptyl-2,3-dihydro-1H-imidazo[4,5-g]quinazoline-2-one (Compound 8)

This compound was synthesized from the compound obtained in Reference Example 9.

$^1$H-NMR(DMSO-d$_6$) δ(ppm): 1.58–1.99(10H, m), 2.25(2H, m), 4.40(1H, m), 4.77(2H, d, J=5.4 Hz), 7.19–7.36(5H, m), 7.40(1H, s), 7.81(1H, s), 8.33(1H, s), 8.59(1H, m), 11.43(1H, s).

EXAMPLE 9

8-benzylamino-3-cyclooctyl-2,3-dihydro-1H-imidazo[4,5-g]quinazoline-2-one (Compound 9)

This compound was synthesized from the compound obtained in Reference Example 10.

$^1$H-NMR(DMSO-$d_6$, 90 MHz) δ(ppm): 1.3–2.0(12H, m), 2.0–2.5(2H, m), 4.3–4.7(1H, m), 4.77(2H, d, J=5.7 Hz), 7.1–7.5(6H, m), 7.81(1H, s), 8.32(1H, s), 8.4–8.65(1H, m).

EXAMPLE 10

3-benzyl-8-benzylamino-2,3-dihydro-1H-imidazo[4,5-g]quinazoline-2-one (Compound 10)

This compound was synthesized from the compound obtained in Reference Example 11.

$^1$H-NMR(DMSO-$d_6$, 90 MHz) δ(ppm): 5.12(4H, d, J=6 Hz), 7.15–7.4(11H, m), 7.58(1H, s), 8.38(1H, s).

EXAMPLE 11

3-ethyl-8-(4-pyridylmethylamino)-2,3-dihydro-1H-imidazo[4,5-g]-2-one dihydrochloride (Compound 11)

This compound was synthesized from the compound obtained in Reference Example 14.

$^1$H-NMR(CD$_3$OD) δ(ppm): 1.35(3H, t, J=7.3 Hz), 3.98 (2H, q, J=7.3 Hz), 7.28 (1H, s), 7.43(2H, d, J=6.3 Hz), 7.77(1H, s), 8.31(1H, s), 8.44(2H, d, J=6.3 Hz) (measured as a free base).

EXAMPLE 12

3-ethyl-8-(3-pyridylmethylamino)-2,3-dihydro-1H-imidazo[4,5-g]quinazoline-2-one dihydrochloride (Compound 12)

This compound was synthesized from the compound obtained in Reference Example 15.

$^1$H-NMR(DMSO-$d_6$) δ(ppm): 1.27(3H, t, J=6.9 Hz), 3.92 (2H, q, J=6.9 Hz), 5.10(2H, d, J=5.4 Hz), 7.61(1H, s), 7.98(1H, dd, J=7.9, 5.4 Hz), 8.32(1H, s), 8.58(1H, d, J=7.9 Hz), 8.82(2H, m), 9.00(1H, s), 11.02(1H, t, J=5.4 Hz), 12.07(1H, s) (measured as a free base).

EXAMPLE 13

3-ethyl-8-(2-pyridylmethylamino)-2,3-dihydro-1H-imidazo[4,5-g]quinazoline-2-one dihydrochloride (Compound 13)

This compound was synthesized from the compound obtained in Reference Example 16.

$^1$H-NMR(DMSO-$d_6$) δ(ppm): 1.25(3H, t, J=6.9 Hz), 3.95 (2H, m), 4.84(2H, d, J=5.4 Hz), 7.26(2H, m), 7.38(1H, s), 7.70(1H, m), 7.86(1H, s), 8.30(1H, s), 8.51(1H, d, J=5.0 Hz), 8.68(1H, t, J=5.9 Hz), 11.46(1H, br).

EXAMPLE 14

3-ethyl-8-(4-methoxybenzylamino)-2,3-dihydro-1H-imidazo[4,5-g]quinazoline-2-one hydrochloride (Compound 14)

This compound was synthesized from the compound obtained in Reference Example 17.

$^1$H-NMR(DMSO-$d_6$) δ(ppm): 1.27(3H, t, J=7.1 Hz), 3.73 (1H, s), 3.94(2H, q, J=7.1 Hz), 4.86(2H, d, J=5.3 Hz), 6.90(2H, d, J=8.5 Hz), 7.34(2H, d, J=8.5 Hz), 8.15(1H, s), 8.80(1H, s), 10.35–10.5(1H, m), 11.98(1H, s).

EXAMPLE 15

3-ethyl-8-(3-methoxybenzylamino)-2,3-dihydro-1H-imidazo[4,5-g]quinazoline-2-one hydrochloride (Compound 15)

This compound was synthesized from the compound obtained in Reference Example 18.

$^1$H-NMR(DMSO-$d_6$) δ(ppm): 1.29(3H, t, J=7.1 Hz), 3.74 (3H, s), 3.95(2H, q, J=7.1 Hz), 4.89(2H, d, J=4.6 Hz), 6.8–6.9(1H, m), 6.9–7.0(2H, m), 7.2–7.3 (1H, m), 7.49(1H, s), 8.15(1H, s), 8.73(1H, s), 10.2–10.3(1H, m), 11.90 (1H, br).

EXAMPLE 16

3-ethyl-8-(2-methoxybenzylamino)-2,3-dihydro-1H-imidazo[4,5-g]quinazoline-2-one hydrochloride (Compound 16)

This compound was synthesized from the compound obtained Reference Example 19.

$^1$H-NMR(DMSO-$d_6$) δ(ppm): 1.28(3H, t, J=7.1 Hz), 3.85 (3H, s), 3.96(2H, q, J=7.1 Hz), 4.88(2H, d, J=5.3 Hz), 6.88(1H, t, J=7.4 Hz), 7.03(1H, d, J=7.9 Hz), 7.18(1H, d, J=7.4 Hz), 7.28(1H, t, J=7.9 Hz), 7.49(1H, s), 8.19(1H, s), 8.78(1H, s), 10.15–10.3(1H, m), 11.97(1H, s).

EXAMPLE 17

3-ethyl-8-(4-methylbenzylamino-2,3-dihydro-1H-imidazo[4,5-g]quinazoline-2-one hydrochloride (Compound 17)

This compound was synthesized from the compound obtained in Reference Example 20.

$^1$H-NMR(DMSO-$d_6$) δ(ppm): 1.28(3H, t, J=7.1 Hz), 2.28 (3H, s), 3.94(2H, q, J=7.1 Hz), 4.88(2H, d, J=5.0 Hz), 7.14(2H, d, J=7.9 Hz), 7.28(2H, d, J=7.9 Hz), 7.48(1H, s), 8.15(1H, s), 8.80(1H, s), 10.4–10.5(1H, m), 11.98(1H, s).

EXAMPLE 18

3-ethyl-8-(3-trifluoromethylbenzylamino)-2,3-dihydro-1H-imidazo[4,5-g]quinazoline-2-one hydrochloride (Compound 18)

This compound was synthesized from the compound obtained in Reference Example 21.

$^1$H-NMR(DMSO-$d_6$) δ(ppm): 1.29(3H, t, J=7.2 Hz), 3.96 (2H, d, J=7.2 Hz), 5.03(1H, d, J=5.4 Hz), 7.49(1H, s), 7.5–7.8(4H, m), 8.17(1H, s), 8.82(1H, s), 10.5–10.6(1H, m), 12.00(1H, s).

EXAMPLE 19

3-ethyl-8-(4-fluorobenzylamino)-2–3-dihydro-1H-imidazo[4,5-g]quinazoline-2-one hydrochloride (Compound 19)

This compound was synthesized from the compound obtained in Reference Example 22.

$^1$H-NMR(DMSO-$d_6$) δ(ppm): 1.28(3H, t, J=7.1 Hz), 3.97 (2H, q, J=7.1 Hz), 4.90(2H, d, J=5.6 Hz), 7.05–7.2(2H, m), 7.4–7.55(3H, m), 8.16(1H, s), 8.80(1H, s), 10.4–10.55(1H, m), 11.98(1H, s).

EXAMPLE 20

8-(3,4-difluorobenzylamino)-3-ethyl-2,3-dihydro-1H-imidazo[4,5-g]quinazoline-2-one hydrochloride (Compound 20)

This compound was synthesized from the compound obtained in Reference Example 23.

$^1$H-NMR(DMSO-d$_6$) δ(ppm): 1.28(3H, t, J=6.9 Hz), 3.95 (2H, q, J=6.9 Hz), 4.91(2H, d, J=4.3 Hz), 7.2–7.6(3H, m), 7.50(1H, s), 8.18(1H, s), 8.81(1H, s), 10.5–10.6(1H, m), 12.00(1H, s ).

EXAMPLE 21

8-(4-chlorobenzylamino)-3-ethyl-2,3-dihydro-1H-imidazo[4,5-g]quinazoline-2-one hydrochloride (Compound 21)

This compound was synthesized from the compound obtained in Reference Example 24.

$^1$H-NMR(DMSO-d$_6$) δ(ppm): 1.27(3H, t, J=7.2 Hz), 3.95 (2H, q, J=7.2 Hz), 4.92(2H, d, J=4.0 Hz), 7.40(2H, d, J=8.6 Hz), 7.42(2H, d, J=8.6 Hz), 7.48(1H, s), 8.15(1H, s), 8.80 (1H, s), 10.45–10.55(1H, m), 12.01(1H, s).

EXAMPLE 22

8-[(N-benzyl-N-methyl)amino]-3-ethyl-2,3-dihydro-1H-imidazo[4-g]quinazoline-2-one hydrochloride (Compound 22)

This compound was synthesized from the compound obtained in Reference Example 25.

$^1$H-NMR(DMSO-d$_6$) δ(ppm): 1.29(3H, t, J=7.1 Hz), 3.57 (3H, s), 3.95(2H, q, J=7.1 Hz), 5.25(2H, s), 7.25–7.45(5H, m), 7.56(1H, s), 7.81(1H, s), 8.78 (1H, s), 11.58(1H, s).

EXAMPLE 23

8-amino-3-ethyl-2,3-dihydro-1H-imidazo[4,5-g]quinazoline-2-one hydrochloride (Compound 23)

This compound was synthesized from the compound obtained in Reference Example 26.

$^1$H-NMR(DMSO-d$_6$) δ(ppm): 1.27(3H, t, J=7.3 Hz), 3.94 (2H, q, J=7.3 Hz), 7.43(1H, s), 7.99(1H, s), 8.71(1H, s), 9.25–9.55(2H, m), 11.91(1H, s).

EXAMPLE 24

3-ethyl-8-ethylamino-2,3-dihydro-1H-imidazo[4,5-g]quinazoline-2-one hydrochloride (Compound 24)

This compound was synthesized from the compound obtained in Reference Example 27.

$^1$H-NMR(DMSO-d$_6$) δ(ppm): 1.27(6H, m), 3.71(2H, m), 3.94(2H, q, J=6.9 Hz), 7.46(1H, s), 8.08(1H, s), 8.79(1H, s), 9.97(1H, br), 11.98(1H, br).

EXAMPLE 25

3-ethyl-8-(indan-1-ylamino)-2,3-dihydro-1H-imidazo[4,5-g]quinazoline-2-one hydrochloride (Compound 25)

This compound was synthesized from the compound obtained in Reference Example 28.

$^1$H-NMR(DMSO-d$_6$) δ(ppm): 1.29(3H, t, J=7.0 Hz), 2.1–2.3(1H, m), 2.5–2.7(1H, m), 2.9–3.2(2H, m), 3.96(2H, q, J=7.0 Hz), 6.22(1H, q, J=7.6 Hz), 7.1–7.4(4H, m), 7.51 (1H, s), 8.18(1H, s), 8.86(1H, s), 10.02(1H, d, J=7.9 Hz), 11.96(1H, s).

EXAMPLE 26

3-ethyl-8-phenylamino-2,3-dihydro-1H-imidazo[4,5-g]quinazoline-2-one hydrochloride (Compound 26)

This compound was synthesized from the compound obtained in Reference Example 29.

$^1$H-NMR(DMSO-d$_6$) δ(ppm): 1.29(3H, t, J=7.4 Hz), 3.96 (2H, q, J=7.4 Hz), 7.30(1H, t, J=7.4 Hz), 7.48(2H, d, J=7.4 Hz), 7.71(2H, d, J=7.4 Hz), 8.43(1H, s), 11.28(1H, br), 12.08(1H, s).

EXAMPLE 27

3-ethyl-8-(2-phenethylamino)-2,3-dihydro-1H-imidazo[4,5-g]quinazoline-2-one hydrochloride (Compound 27)

This compound was synthesized from the compound obtained in Reference Example 30.

$^1$H-NMR(DMSO-d$_6$) δ(ppm): 1.26(3H, t, J=6.9 Hz), 3.01 (2H, t, J=7.4 Hz), 3.19(2H, m), 3.93(2H, q, J=6.9 Hz), 7.19–7.33(5H, m), 7.39(1H, s), 8.00(1H, s), 8.80(1H, s), 9.91(1H, br), 11.94(1H, br).

EXAMPLE 28

3-ethyl-8-(1-naphthylmethylamino)-2,3-dihydro-1H-imidazo[4,5-g]quinazoline-2-one hydrochloride (Compound 28)

This compound was synthesized from the compound obtained in Reference Example 31.

$^1$H-NMR(DMSO-d$_6$) δ(ppm): 1.27(3H, t, J=6.9 Hz), 3.96 (2H, q, J=6.9 Hz), 5.39(2H, d, J=5.0 Hz), 7.46(2H, m), 7.50(1H, s), 7.58(2H, m), 7.90(1H, m), 7.99(1H, m), 8.17 (1H, s), 8.83(1H, s), 10.35(1H, br), 11.97(1H, br).

EXAMPLE 29

8-diphenylmethylamino-3-ethyl-2,3-dihydro-1H-imidazo[4,5-g]quinazoline-2-one hydrochloride (Compound 29)

This compound was synthesized from the compound obtained in Reference Example 32.

$^1$H-NMR(DMSO-d$_6$) δ(ppm): 1.28(3H, t, J=7.3 Hz), 3.95 (2H, q, J=7.3 Hz), 7.0–7.1(1H, m), 7.3–7.5(10H, m), 7.51 (1H, s), 8.39(1H, s), 8.84(1H, s), 10.37(1H, d, J=8.2 Hz), 12.01(1H, s).

EXAMPLE 30

3-ethyl-8-(2,3,4,5-tetrahydro-2-furylmethylamino)-2,3-dihydro-1H-imidazo[4,5-g]quinazoline-2-one hydrochloride (Compound 30)

This compound was synthesized from the compound obtained in Reference Example 33.

$^1$H-NMR(DMSO-d$_6$) δ(ppm): 1.24(3H, m), 1.88(4H, m), 3.61(3H, m), 3.80(1H, m), 3.94(2H, m), 4.13(1H, m), 7.33 (1H, s), 7.80(1H, s), 8.07(1H, m), 8.32(1H, s), 11.37(1H, br) (measured as a free base).

EXAMPLE 31

3-ethyl-8-(4-phenylpiperazin-1-yl)-2,3-dihydro-1H-imidazo[4,5-g]quinazoline-2-one dihydrochloride (Compound 31)

This compound was synthesized from the compound obtained in Reference Example 35.

$^1$H-NMR(DMSO-d$_6$) δ(ppm): 1.27(3H, t, J=7.3 Hz), 3.35–3.5(4H, m), 3.95(2H, q, J=7.3 Hz), 4.2–4.4(4H, m), 6.84(1H, t, J=7.3 Hz), 7.00(2H, d, J=7.9 Hz), 7.27(2H, dd, J=7.9, 7.3 Hz), 7.53(1H, s), 7.68(1H, s), 8.81(1H, s), 11.68 (1H, s).

EXAMPLE 32

8-(4-benzylpiperazin-1-yl)-3-ethyl-2,3-dihydro-1H-imidazo[4,5-g]quinazoline-2-one dihydrochloride (Compound 32)

This compound was synthesized from the compound obtained in Reference Example 36.

$^1$H-NMR(DMSO-d$_6$) δ(ppm): 1.26(3H, t, J=7.2 Hz), 3.2–3.8(4H, m), 3.95(2H, q, J=7.2 Hz), 3.9–4.2(2H, m), 4.38(2H, s), 4.6–4.8(2H, m), 7.45–7.55(3H, m), 7.57(1H, s), 7.60(1H, s), 7.6–7.7(2H, m), 8.86(1H, s), 11.68(1H, s), 11.9–12.2(1H, br).

EXAMPLE 33

8-(4-benzylpiperidino)-3-ethyl-2,3-dihydro-1H-imidazo[4,5-g]quinazoline-2-one hydrochloride (Compound 33)

This compound was synthesized from the compound obtained in Reference Example 37.

$^1$H-NMR(DMSO-d$_6$) δ(ppm): 1.26(3H, t, J=7.2 Hz), 1.3–1.55(2H, m), 1.7–1.9 (2H, m), 1.9–2.2(1H, m), 2.55–2.7 (2H, m), 3.3–3.6(2H, m), 3.93(2H, q, J=7.2 Hz), 4.6–4.7(2H, m), 7.15–7.4(5H, m), 7.50(1H, s), 7.51(1H, s), 8.72 (1H, s), 11.57(1H, s).

EXAMPLE 34

3-ethyl-8-piperidino-2,3-dihydro-1H-imidazo[4,5-g] quinazoline-2-one hydrochloride (Compound 34)

This compound was synthesized from the compound obtained in Reference Example 38.

$^1$H-NMR(DMSO-d$_6$) δ(ppm): 1.26(3H, t, J=7.3 Hz), 1.76 (6H, br s), 3.94(2H, q, J=7.3 Hz), 4.06(4H, br), 7.51(1H, s), 7.54(1H, s), 8.73(1H, s), 11.63 (1H, s).

EXAMPLE 35

8-[N-(2-dimethylaminoethyl)-N-methylamino]-3-ethyl-2,3-dihydro-1H-imidazo[4,5-g]quinazoline-2-one dihydrochloride (Compound 35)

This compound was synthesized from the compound obtained in Reference Example 39.

$^1$H-NMR(DMSO-d$_6$) δ(ppm): 1.27(3H, t, J=7.2 Hz), 2.89 (6H, s), 3.53(2H, t, J=6.3 Hz), 3.68(3H, s), 3.95(2H, q, J=7.2 Hz), 4.32(2H, t, J=6.3 Hz), 7.54(1H, s), 7.94(1H, s), 8.76 (1H, s).

EXAMPLE 36

3-ethyl-8-(4-methylhomopiperazin-1-yl)-2,3-dihydro-1H-imidazo[4,5-g]quinazoline-2-one dihydrochloride (Compound 36)

This compound was synthesized from the compound obtained in Reference Example 40.

$^1$H-NMR(DMSO-d$_6$) δ(ppm): 1.27(3H, t, J=7.2 Hz), 2.15–2.30(1H, m), 2.5–2.7(1H, m), 2.75(3H, br), 3.1–3.3 (2H, m), 3.4–3.6(1H, m), 3.6–3.8(1H, m), 3.95(2H, q, J=7.2 Hz), 4.0–4.2(2H, m), 4.3–4.5(1H, m), 4.5–4.7(1H, m), 7.55 (1H, s), 7.69(1H, s), 8.79(1H, s), 11.1–11.3(1H, br), 11.62 (1H, s).

EXAMPLE 37

8-(bicyclo[2.2.1]heptan-2-ylamino)-3-ethyl-2,3-dihydro-1H-imidazo[4,5-g]quinazoline-2-one hydrochloride (Compound 37)

This compound was synthesized from the compound obtained in Reference Example 41.

$^1$H-NMR(DMSO-d$_6$) δ(ppm): 1.15–1.35(3H, m), 1.30 (3H, t, J=7.1 Hz), 1.5–1.7(2H, m), 1.7–1.8(1H, m), 1.8–1.9 (2H, m), 2.37(2H, br), 3.95(2H, q, J=7.1 Hz), 4.15–4.30(1H, m), 7.44(1H, s), 8.31(1H, s), 8.79(1H, s), 9.19(1H, br d, J=5.7 Hz), 11.92(1H, s).

EXAMPLE 38

8-cyclohexylmethyl$^{amino}$-3-ethyl-2,3-dihydro-1H-imidazo[4,5-g]quinazoline-2-one hydrochloride (Compound 38)

This compound was synthesized from the compound obtained in Reference Example 42.

$^1$H-NMR(DMSO-d$_6$) δppm): 0.89–1.18(5H, m), 1.23(3H, t, J=6.9 Hz), 1.67–1.77(6H, m), 3.91(2H, q, J=6.9 Hz), 7.32(1H, s), 7.79(1H, s), 8.01(1H, m), 8.32(1H, s), 11.36 (1H, br) (measured as a free base).

EXAMPLE 39

8-benzylamino-3-ethyl-2,3-dihydro-1H-imidazo[4,5-g]quinazoline-2-thione (Compound 39)

6-Amino-4-benzylamino-7-ethylaminoquinazoline (4.5 g, 15.4 mmol) obtained, according to the procedures in Example 1, from 4-benzylamino-7-ethylamino-6-nitroquinazoline obtained in Reference Example 3 was suspended in ethanol (300 ml). To the suspension were added carbon disulfide (25 ml) and triethylamine (9.3 ml, 66.4 mmol), followed by heating under reflux for 6.5 hours. Water was added to the reaction mixture and the resulting crystals were filtered and recrystallized from a mixed solvent of dimethylformamide and ethanol to give the title compound (3.54 g, 60.6%).

$^1$H-NMR(DMSO-d$_6$, 90 MHz) δ(ppm): 1.27(3H, t, J=7.2 Hz), 4.34(2H, q, J=7.2 Hz), 4.77(2H, d, J=5.4 Hz), 7.2–7.5 (5H, m), 7.60(1H, s), 8.06(1H, s), 8.37(1H, s), 8.8–9.0(1H, m), 13.1–13.4(1H, br).

The following compounds of Examples 40 to 75, Examples 90 to 102, Examples 104 to 112, Example 114 and Example 115 were prepared according to a manner similar to that in Example 39 except for using the corresponding nitro compounds obtained in Reference Examples in place of 4-benzylamino-7-ethylamino-6-nitroquinazoline.

EXAMPLE 40

8-benzylamino-3-methyl-2,3-dihydro-1H-imidazo[4,5-g]quinazoline-2-thione (Compound 40)

This compound was synthesized from the compound obtained in Reference Example 2.

$^1$H-NMR(DMSO-d$_6$, 90 MHz) δ(ppm): 3.73(3H, s), 4.86 (2H, d, J=5.4 Hz), 7.2–7.5(6H, m), 8.07(1H, s), 8.41(1H, s), 8.6–8.8(1H, m).

EXAMPLE 41

8-benzylamino-3-isopropyl-2,3-dihydro-1H-imidazo [4,5-g]quinazoline-2-thione (Compound 41)

This compound was synthesized from the compound obtained in Reference Example 4.

¹H-NMR(DMSO-d₆) δ(ppm): 1.56(6H, d, J=6.9 Hz), 4.79 (2H, d, J=5.9 Hz), 5.48(1H, m), 7.20–7.44(5H, m), 7.74(1H, s), 8.09(1H, s), 8.38(1H, s), 8.87 (1H, m), 13.31(1H, s).

EXAMPLE 42

8-benzylamino-3-(n-propyl)-2,3-dihydro-1H-imidazo[4,5-g]quinazoline-2-thione (Compound 42)

This compound was synthesized from compound A obtained in Reference Example 5.

¹H-NMR(DMSO-d₆) δ(ppm): 0.94(3H, t, J=7.4 Hz), 4.27 (2H, t, J=7.4, 6.9 Hz), 4.79(2H, d, J=5.4 Hz), 7.23–7.38(5H, m), 7.66(1H, s), 8.08(1H, s), 8.38 (1H, s), 8.86(1H, m).

EXAMPLE 43

8-benzylamino-3-(n-butyl)-2,3-dihydro-1H-imidazo[4,5-g]quinazoline-2-thione (Compound 43)

This compound was synthesized from the compound obtained in Reference Example 6.

¹H-NMR(DMSO-d₆) δ(ppm): 0.90(3H, m), 1.21(2H, m), 1.74(2H, m), 4.31(2H, m), 4.79(2H, d, J=5.4 Hz), 7.20–7.39 (5H, m), 7.63(1H, s), 8.09(1H, s), 8.38(1H, s), 8.88(1H, m), 13.26(1H, m).

EXAMPLE 44

8-benzylamino-3-cyclohexyl-2,3-dihydro-1H-imidazo[4,5-g]quinazoline-2-thione (Compound 44)

This compound was synthesized from the compound obtained in Reference Example 8.

¹H-NMR(DMSO-d₆, 90 MHz) δ(ppm): 1.3–2.0(10H, m), 4.79(2H, d, J=5.5 Hz), 4.9–5.2(1H, m), 7.2–7.4(5H, m), 7.77(1H, s), 8.07(1H, s), 8.38(1H, s), 8.7–8.9(1H, m).

EXAMPLE 45

8-benzylamino-3-cycloheptyl-2,3-dihydro-1H-imidazo[4,5-g]quinazoline-2-thione (Compound 45)

This compound was synthesized from the compound obtained in Reference Example 9.

¹H-NMR(DMSO-d₆) δ(ppm): 1.58–1.98(10H, m), 2.29 (2H, m), 4.88(2H, d, J=5.9 Hz), 5.36(1H, m), 7.22–7.41(5H, m), 7.67(1H, s), 8.04(1H, s), 8.38(1H, s), 8.49(1H, s), 12.94(1H, s).

EXAMPLE 46

8-benzylamino-3-cyclooctyl-2,3-dihydro-1H-imidazo[4,5-g]quinazoline-2-thione (Compound 46)

This compound was synthesized from the compound obtained in Reference Example 10.

¹H-NMR(CDCl₃+DMSO-d₆, 90 MHz) δ(ppm): 1.5–1.9 (14H, m), 4.87(2H, d, J=5 Hz), 5.3–5.6(1H, m), 7.15–7.35 (5H, m), 7.57(1H, s), 7.94(1H, s), 8.47(1H, s).

EXAMPLE 47

3-ethyl-8-(4-pyridylmethylamino)-2,3-dihydro-1H-imidazo[4,5-g]quinazoline-2-thione dihydrochloride (Compound 47)

This compound was synthesized from the compound obtained in Reference Example 14.

¹H-NMR(DMSO-d₆) δ(ppm): 1.31(3H, t, J=7.3 Hz), 4.29 (2H, m), 5.14(2H, m), 7.76(1H, d, J=5.9 Hz), 7.91(2H, m), 8.43(1H, d, J=5.9 Hz), 8.80(2H, m), 8.84(1H, s), 10.93(1H, br), 13.82(1H, s).

EXAMPLE 48

3-ethyl-8-(3-pyridylmethylamino)-2,3-dihydro-1H-imidazo[4,5-g]quinazoline-2-thione dihydrochloride (Compound 48)

This compound was synthesized from the compound obtained in Reference Example 15.

¹H-NMR(DMSO-d₆) δ(ppm): 1.27(3H, t, J=7.3 Hz), 3.93 (2H, q, J=7.3 Hz), 5.07(2H, d, J=5.6 Hz), 7.66(1H, s), 7.91(1H, dd, J=7.9, 5.3 Hz), 8.38(1H, s), 8.51(1H, m), 8.77(1H, m), 8.80(1H, s), 8.96(1H, s), 11.20(1H, m), 12.11 (1H, br).

EXAMPLE 49

3-ethyl-8-(2-pyridylmethylamino)-2,3-dihydro-1H-imidazo[4,5-g]quinazoline-2-thione dihydrochloride (Compound 49)

This compound was synthesized from the compound obtained in Reference Example 16.

¹H-NMR(DMSO-d₆) δ(ppm): 1.29(3H, t, J=6.9 Hz), 4.36 (2H, q, J=6.9 Hz), 4.85(2H, d, J=5.4 Hz), 7.28(2H, m), 7.70(2H, m), 8.12(1H, s), 8.36(1H, s), 8.52(1H, m), 8.95 (1H, m), 13.28(1H, br) (measured as a free base).

EXAMPLE 50

3-ethyl-8-(4-methoxybenzylamino)-2,3-dihydro-1H-imidazo[4,5-g]quinazoline-2-thione hydrochloride (Compound 50)

This compound was synthesized from the compound obtained in Reference Example 17.

¹H-NMR(DMSO-d₆) δ(ppm): 1.30(3H, t, J=7.0 Hz), 3.73 (3H, s), 4.34(2H, q, J=7.0 Hz), 4.88(2H, d, J=5.0 Hz), 6.90(2H, d, J=8.4 Hz), 7.35(2H, d, J=8.4 Hz), 7.73(1H, s), 8.37(1H, s), 8.86(1H, s), 10.6–10.7(1H, m), 13.79(1H, s).

EXAMPLE 51

3-ethyl-8-(3-methoxybenzylamino)-2,3-dihydro-1H-imidazo[4,5-g]quinazoline-3-thione hydrochloride (Compound 51)

This compound was synthesized from the compound obtained in Reference Example 18.

¹H-NMR(DMSO-d₆) δ(ppm): 1.34(3H, t, J=7.0 Hz), 3.75 (3H, s), 4.36(2H, q, J=7.0 Hz), 4.93(2H, s), 6.8–6.9(1H, m), 6.9–7.0(2H, m), 7.2–7.3(1H, m), 7.70(1H, s), 8.37(1H, s), 8.85(1H, s), 10.55–10.65(1H, m), 13.71(1H, s).

EXAMPLE 52

3-ethyl-8-(2-methoxybenzylamino)-2,3-dihydro-1H-imidazo[4,5-g]quinazoline-2-thione hydrochloride (Compound 52)

This compound was synthesized from the compound obtained in Reference Example 19.

¹H-NMR(DMSO-d₆) δ(ppm): 1.31(3H, t, J=7.1 Hz), 3.85 (3H, s), 4.36(2H, q, J=7.1 Hz), 4.90(2H, d, J=4.9 Hz), 6.89(1H, t, J=7.6 Hz), 7.04(1H, d, J=8.3 Hz), 7.21(1H, d, J=7.6 Hz), 7.29(1H, t, J=8.3 Hz), 7.72(1H, s), 8.42(1H, s), 8.83(1H, s), 10.45–10.55(1H, m), 13.73(1H, s).

EXAMPLE 53

3-ethyl-8-(4-methylbenzylamino)-2,3-dihydro-1H-imidazo[4,5-g]quinazoline-2-thione hydrochloride (Compound 53)

This compound was synthesized from the compound obtained in Reference Example 20.

$^1$H-NMR(DMSO-d$_6$) δ(ppm): 1.31(3H, t, J=7.1 Hz), 2.29 (1H, s), 4.35(2H, q, J=7.1 Hz), 4.90(2H, d, J=5.3 Hz), 7.15(2H, d, J=7.9 Hz), 7.29(2H, d, J=7.9 Hz), 7.72(1H, s), 8.37(1H, s), 8.85(1H, s), 10.6–10.7(1H, m), 13.73(1H, s).

EXAMPLE 54

3-ethyl-8-(3-trifluoromethylbenzylamino)-2,3-dihydro-1H-imidazo[4,5-g]quinazoline-2-thione hydrochloride (Compound 54)

This compound was synthesized from the compound obtained in Reference Example 21.

$^1$H-NMR(DMSO-d$_6$) δ(ppm): 1.32(3H, t, J=7.2 Hz), 4.37 (2H, q, J=7.2 Hz), 5.05(1H, br s), 7.5–7.8(5H, m), 8.34(1H, s), 8.88(1H, s), 10.6–10.7(1H, m), 13.74(1H, s).

EXAMPLE 55

3-ethyl-8-(4-fluorobenzylamino)-2,3-dihydro-1H-imidazo[4,5-g]quinazoline-2-thione hydrochloride (Compound 55)

This compound was synthesized from the compound obtained in Reference Example 22.

$^1$H-NMR(DMSO-d$_6$) δ(ppm): 1.31(3H, t, J=6.9 Hz), 4.35 (2H, q, J=6.9 Hz), 4.91(2H, d, J=5.0 Hz), 7.1–7.25(2H, m), 7.4–7.5(2H, m), 7.71(1H, s), 8.34(1H, s), 8.82(1H, s), 10.45–10.6(1H, m), 13.70(1H, s).

EXAMPLE 56

8-(3,4-difluorobenzylamino)-3-ethyl-2,3-dihydro-1H-imidazo[4,5-g]quinazoline-2-thione hydrochloride (Compound 56)

This compound was synthesized from the compound obtained in Reference Example 23.

$^1$H-NMR(DMSO-d$_6$) δ(ppm): 1.31(3H, t, J=6.9 Hz), 4.36 (2H, q, J=6.9 Hz), 4.93(2H, d, J=5.2 Hz), 7.2–7.6(3H, m), 7.74(1H, s), 8.38(1H, s), 8.86(1H, s), 10.65–10.8(1H, m), 13.75(1H, s).

EXAMPLE 57

8-(4-chlorobenzylamino)-3-ethyl-2,3-dihydro-1H-imidazo[4,5-g]quinazoline-2-thione hydrochloride (Compound 57)

This compound was synthesized from the compound obtained in Reference Example 24.

$^1$H-NMR(DMSO-d$_6$) δ(ppm): 1.31(3H, t, J=7.1 Hz), 4.36 (2H, q, J=7.1 Hz), 4.93(2H, d, J=4.6 Hz), 7.41(2H, d, J=8.6 Hz), 7.43(2H, d, J=8.6 Hz), 7.71(1H, s), 8.36(1H, s), 8.86 (1H, s), 10.65–10.75(1H, m), 13.75(1H, s).

EXAMPLE 58

8-[(N-benzyl-N-methyl)amino]-3-ethyl-2,3-dihydro-1H-imidazo[4,5-g]quinazoline-2-thione hydrochloride (Compound 58)

This compound was synthesized from the compound obtained in Reference Example 25.

$^1$H-NMR(DMSO-d$_6$) δ(ppm): 1.31(3H, t, J=6.9 Hz), 3.59 (3H, s), 4.35(2H, q, J=6.9 Hz), 5.27(2H, s), 7.25–7.5(5H, m), 7.78(1H, s), 7.99(1H, s), 8.82(1H, s), 13.37(1H, s).

EXAMPLE 59

8-amino-3-ethyl-2,3-dihydro-1H-imidazo[4,5-g]quinazoline-2-thione hydrochloride (Compound 59)

This compound was synthesized from the compound obtained in Reference Example 26.

$^1$H-NMR(DMSO-d$_6$) δ(ppm): 1.31(3H, t, J=7.1 Hz), 4.36 (2H, q, J=7.1 Hz), 7.68(1H, s), 8.25(1H, s), 8.75(1H, s), 9.45–9.65(1H, br), 9.65–9.85(1H, br), 13.67(1H, s).

EXAMPLE 60

3-ethyl-8-ethylamino-2,3-dihydro-1H-imidazo[4,5-g]quinazoline-2-thione hydrochloride (Compound 60)

This compound was synthesized from the compound obtained in Reference Example 27.

$^1$H-NMR(DMSO-d$_6$) δ(ppm): 1.26(6H, t, J=6.9 Hz), 3.56 (2H, dq, J=6.9, 5.4 Hz), 4.34(2H, q, J=6.9 Hz), 7.61(1H, s), 8.01(1H, s), 8.28(1H, m), 8.39(1H, s), 13.24(1H, br) (measured as a free base).

EXAMPLE 61

3-ethyl-8-(indan-1-ylamino)-2,3-dihydro-1H-imidazo[4,5-g]quinazoline-2-thione hydrochloride (Compound 61)

This compound was synthesized from the compound obtained in Reference Example 28.

$^1$H-NMR(DMSO-d$_6$) δ(ppm): 1.33(3H, t, J=7.0 Hz), 2.1–2.3(1H, m), 2.5–2.7(1H, m), 2.9–3.2(2H, m), 4.37(1H, q, J=7.0 Hz), 6.25(1H, q, J=7.6 Hz), 7.15–7.4(4H, m), 7.73(1H, s), 8.41(1H, s), 8.92(1H, s), 10.29(1H, d, J=7.4 Hz), 13.71(1H, s).

EXAMPLE 62

3-ethyl-8-phenylamino-2,3-dihydro-1H-imidazo[4,5-g]quinazoline-2-thione hydrochloride (Compound 62)

This compound was synthesized from the compound obtained in Reference Example 29.

$^1$H-NMR(DMSO-d$_6$) δ(ppm): 1.31(3H, t, J=6.9 Hz), 4.38 (2H, q, J=6.9 Hz), 7.12(1H, dd, J=7.4, 7.4 Hz), 7.39(1H, dd, J=7.4, 7.4 Hz), 7.74(1H, s), 7.85(1H, d, J=7.9 Hz), 8.35(1H, s), 8.52(1H, s), 9.86(1H, s), 13.35(1H, s) (measured as a free base).

EXAMPLE 63

3-ethyl-8-(2-phenethylamino)-2,3-dihydro-1H-imidazo[4,5-g]quinazoline-2-thione hydrochloride (Compound 63)

This compound was synthesized from the compound obtained in Reference Example 30.

$^1$H-NMR(DMSO-d$_6$) δ(ppm): 1.29(3H, t, J=6.9 Hz), 3.02 (2H, m), 3.91(2H, m), 4.35(2H, m), 7.19–7.34(5H, m) 7.62(1H, s), 8.23(1H, s), 8.84(1H, s), 10.09(1H, br), 13.70 (1H, br).

EXAMPLE 64

3-ethyl-8-(1-naphthylmethylamino)-2,3-dihydro-1H-imidazo[4,5-g]quinazoline-2-thione hydrochloride (Compound 64)

This compound was synthesized from the compound obtained in Reference Example 31.

¹H-NMR(DMSO-d₆) δ(ppm): 1.30(3H, t, J=6.9 Hz), 4.36 (2H, m), 5.41(1H, d, J=5.3 Hz), 7.46–7.64(4H, m), 7.70(1H, s), 7.91(1H, m), 8.00(1H, m), 8.20 (1H, m), 8.41(1H, s), 8.88(1H, s), 10.59(1H, br), 13.73(1H, br).

EXAMPLE 65

8-diphenylmethylamino-3-ethyl-2,3-dihydro-1H-imidazo[4,5-g]quinazoline-2-thione hydrochloride (Compound 65)

This compound was synthesized from the compound obtained in Reference Example 32.

¹H-NMR(DMSO-d₆) δ(ppm): 1.31(3H, t, J=6.9 Hz), 4.37 (2H, q, J=6.9 Hz), 7.05–7.10(1H, m), 7.3–7.5(10H, m), 7.69(1H, s), 8.60(1H, s), 8.87(1H, s), 10.55(1H, d, J=6.9 Hz), 13.71(1H, s).

EXAMPLE 66

3-ethyl-8-(2,3,4,5-tetrahydro-2-furylmethylamino)-2,3-dihydro-1H-imidazo[4,5-g]quinazoline-2-thione hydrochloride (Compound 66)

This compound was synthesized from the compound obtained in Reference Example 33.

¹H-NMR(DMSO-d₆) δ(ppm): 1.28(3H, t, J=6.9 Hz), 1.57–2.01(4H, m), 3.62(3H, m), 3.81(1H, m), 4.15(1H, m), 4.34(2H, q, J=6.9 Hz), 7.61(1H, s), 8.06(1H, s), 8.37(1H, br), 8.38(1H, s), 13.23(1H, br) (measured as a free base).

EXAMPLE 67

3-ethyl-8-(thienylmethylamino)-2,3-dihydro-1H-imidazo[4,5-g]quinazoline-2-thione hydrochloride (Compound 67)

This compound was synthesized from the compound obtained in Reference Example 34.

¹H-NMR(DMSO-d₆) δ(ppm): 1.29(3H, t, J=6.9 Hz), 4.35 (2H, q, J=6.9 Hz), 4.94(2H, d, J=4.9 Hz), 6.96(1H, dd, J=4.5, 4.0 Hz), 7.08(1H, d, J=4.0 Hz), 7.36(1H, d, J=4.5 Hz), 7.65(1H, s), 8.03(1H, s), 8.48(1H, s), 9.02(1H, br), 13.29 (1H, br).

EXAMPLE 68

3-ethyl-8-(4-phenylpiperazin-1-yl)-2,3-dihydro-1H-imidazo[4,5-g]quinazoline-2-thione dihydrochloride (Compound 68)

This compound was synthesized from the compound obtained in Reference Example 35.

¹H-NMR(DMSO-d₆) δ(ppm): 1.30(3H, t, J=7.2 Hz), 3.4–3.7(4H, m), 4.2–4.4(6H, m), 6.82(1H, t, J=7.3 Hz), 6.97(2H, d, J=7.9 Hz), 7.27(2H, dd, J=7.9, 7.3 Hz), 7.73(1H, s), 7.85(1H, s), 8.82(1H, s), 13.40(1H, s).

EXAMPLE 69

8-(4-benzylpiperazin-1-yl)-3-ethyl-2,3-dihydro-1H-imidazo[4,5-g]quinazoline-2-thione dihydrochloride (Compound 69)

This compound was synthesized from the compound obtained in Reference Example 36.

¹H-NMR(DMSO-d₆) δ(ppm): 1.30(3H, t, J=7.1 Hz), 3.2–3.8(4H, m), 4.0–4.2(2H, m), 4.3–4.5(4H, m), 4.6–4.8 (2H, m), 7.4–7.5(3H, m), 7.7–7.8(2H, m), 7.76(1H, s), 7.82(1H, s), 8.88(1H, s), 11.9–12.2(1H, br), 13.41(1H, s).

EXAMPLE 70

8-(4-benzylpiperidino)-3-ethyl-2,3-dihydro-1H-imidazo[4,5-g]quinazoline-2-thione hydrochloride (Compound 70)

This compound was synthesized from the compound obtained in Reference Example 37.

¹H-NMR(DMSO-d₆) δ(ppm): 1.29(3H, t, J=7.2 Hz), 1.3–1.6(2H, m), 1.7–1.9(2H, m), 1.9–2.2(1H, m), 2.6–2.7 (2H, m), 3.3–3.6(2H, m), 4.34(2H, q, J=7.2 Hz), 4.65–4.80 (2H, m), 7.15–7.4(5H, m), 7.72(1H, s), 8.75(1H, s), 13.32 (1H, s).

EXAMPLE 71

3-ethyl-8-piperidino-2,3-dihydro-1H-imidazo[4,5-g] quinazoline-2-thione hydrochloride (Compound 71)

This compound was synthesized from the compound obtained in Reference Example 38.

¹H-NMR(DMSO-d₆) δ(ppm): 1.30(3H, t, J=7.1 Hz), 1.77 (6H, br), 4.09(4H, br), 4.34(2H, q, J=7.1 Hz), 7.72(1H, s), 7.74(1H, s), 8.76(1H, s), 13.37(1H, s).

EXAMPLE 72

8-[N-(2-dimethylaminoethyl)-N-methylamino]-3-ethyl-2,3-dihydro-1H-imidazo[4,5-g]quinazoline-2-thione dihydrochloride (Compound 72)

This compound was synthesized from the compound obtained in Reference Example 39.

¹H-NMR(DMSO-d₆) δ(ppm): 1.31(3H, t, J=7.1 Hz), 2.92 (6H, s), 3.54(2H, t, J=6.0 Hz), 3.72(3H, s), 4.3–4.4(4H, m), 7.70(1H, s), 8.12(1H, s), 8.76(1H, s).

EXAMPLE 73

3-ethyl-8-(4-methylhomopiperazin-1-yl)-2,3-dihydro-1H-imidazo[4,5-g]quinazoline-2-thione dihydrochloride (Compound 73)

This compound was synthesized from the compound obtained in Reference Example 40

¹H-NMR(DMSO-d₆) δ(ppm): 1.30(3H, t, J=7.2 Hz), 2.1–2.4(1H, m), 2.6–2.9(4H, m), 3.1–3.8(4H, m), 4.0–4.3 (2H, m), 4.35(2H, q, J=7.2 Hz), 4.3–4.5(1H, m), 4.5–4.7(1H, m), 7.83(1H, s), 7.90(1H, s), 8.83(1H, s), 11.4–11.6(1H, br), 13.42(1H, s).

EXAMPLE 74

8-(bicyclo[2.2.1]heptan-2-ylamino)-3-ethyl-2,3-dihydro-1H-imidazo[4,5-g]quinazoline-2-thione hydrochloride (Compound 74)

This compound was synthesized from the compound obtained in Reference Example 41.

¹H-NMR(DMSO-d₆) δ(ppm): 1.15–1.35(3H, m), 1.32 (3H, t, J=7.1 Hz), 1.45–1.7(2H, m), 1.7–1.8(1H, m), 1.8–1.9 (2H, m), 2.3–2.5(2H, m), 4.2–4.3(1H, m), 4.35(2H, q, J=7.1 Hz), 7.68(1H, s), 8.52(1H, s), 8.84(1H, s), 9.44(1H, d, J=5.9 Hz), 13.66(1H, s).

EXAMPLE 75

8-cyclohexylmethylamino-3-ethyl-2,3-dihydro-1H-imidazo[4,5-g]quinazoline-2-thione hydrochloride (Compound 75)

This compound was synthesized from the compound obtained in Reference Example 42.

¹H-NMR(DMSO-d₆) δ(ppm): 0.99–1.23(5H, m), 1.29 (3H, t, J=6.9 Hz), 1.64–1.77(6H, m), 3.56(2H, m), 4.35(2H, q, J=6.9 Hz), 7.68(1H, s), 8.35(1H, s), 8.82(1H, s), 10.15 (1H, br), 13.74(1H, br).

EXAMPLE 76

3-ethyl-8-(3-morpholinopropylamino)-2,3-dihydro-1H-imidazo[4,5-g]quinazoline-2-one dihydrochloride (Compound 76)

This compound was synthesized from the compound obtained in Reference Example 43.

¹H-NMR(DMSO-d₆) δ(ppm): 1.27(3H, t, J=7.1 Hz), 2.05–2.25(2H, m), 2.9–3.3(6H, m), 3.7–4.0(8H, m), 7.46 (1H, s), 8.10(1H, s), 8.82(1H, s), 10.05–10.15(1H, br), 10.9–11.1(1H, br), 11.98(1H, s).

EXAMPLE 77

3-ethyl-8-(2-morpholinoethylamino)-2,3-dihydro-1H-imidazo[4,5-g]quinazoline-2-one dihydrochloride (Compound 77)

This compound was synthesized from the compound obtained in Reference Example 44.

¹H-NMR(DMSO-d₆) δ(ppm): 1.28(3H, t, J=7.1 Hz), 3.4–3.6(6H, m), 3.8–4.05 (6H, m), 4.05–4.2(2H, m), 7.48 (1H, s), 8.14(1H, s), 8.86(1H, s), 10.1–10.3(1H, br), 10.9–11.3(1H, br), 11.99(1H, s).

EXAMPLE 78

3-ethyl-8-[2-(3-pyridyl)ethylamino]-2,3-dihydro-1H-imidazo[4,5-g]quinazoline-2-one dihydrochloride (Compound 78)

This compound was synthesized from the compound obtained in Reference Example 45.

¹H-NMR(DMSO-d₆) δ(ppm): 1.27(3H, t, J=7.1 Hz), 3.25 (2H, t, J=6.4 Hz), 3.94(2H, q, J=7.1 Hz), 4.0–4.1(2H, m), 7.50(1H, s), 7.89(1H, dd, J=7.9, 5.3 Hz), 8.08(1H, s), 8.41(1H, d, J=7.9 Hz), 8.75(1H, d, J=5.3 Hz), 8.78(1H, s), 8.88(1H, br), 10.05–10.15(1H, m), 11.97(1H, s).

EXAMPLE 79

3-ethyl-8-[2-(2-pyridyl)ethylamino]-2,3-dihydro-1H-imidazo[4,5-g]quinazoline-2-one dihydrochloride (Compound 79)

This compound was synthesized from the compound obtained in Reference Example 46.

¹H-NMR(DMSO-d₆) δ(ppm): 1.28(3H, t, J=7.1 Hz), 3.3–3.5(2H, m), 3.95(2H, q, J=7.1 Hz), 4.1–4.2(2H, m), 7.45(1H, s), 7.7–7.9(2H, m), 8.00(1H, s)f 8.2–8.3(1H, m), 8.65–8.75(1H, m), 8.76(1H, s), 10.0–10.1(1H, m), 11.94 (1H, s).

EXAMPLE 80

3-ethyl-8-[2-(4-pyridyl)ethylamino]-2,3-dihydro-1H-imidazo[4,5-g]quinazoline-2-one dihydrochloride (Compound 80)

This compound was synthesized from the compound obtained in Reference Example 47.

¹H-NMR(DMSO-d₆) δ(ppm): 1.27(3H, t, J=7.1 Hz), 3.35 (2H, t, J=6.4 Hz), 3.94(2H, q, J=7.1 Hz), 4.05–4.15(2H, m), 7.52(1H, s), 7.98(2H, d, J=6.3 Hz), 8.12(1H, s), 8.80(1H, s), 8.81(2H, d, J=6.3 Hz), 10.1–10.25(1H, m), 11.98(1H, s).

EXAMPLE 81

3-ethyl-8-[2-(1-pyrrolidinyl)ethylamino]-2,3-dihydro-1H-imidazo[4,5-g]quinazoline-2-one dihydrochloride (Compound 81)

This compound was synthesized from the compound obtained in Reference Example 48.

¹H-NMR(DMSO-d₆) δ(ppm): 1.28(3H, t, J=6.9 Hz), 1.8–2.1(4H, m), 3.0–3.2(2H, m), 3.5–3.6(2H, m), 3.6–3.8 (2H, m), 3.95(2H, q, J=6.9 Hz), 4.0–4.15(2H, m), 7.52(1H, s), 8.18(1H, s), 8.85(1H, s), 10.15–10.3(1H, br), 10.7–10.9 (1H, br), 11.99(1H, s).

EXAMPLE 82

3-ethyl-8-(2-piperidinoethylamino)-2,3-dihydro-1H-imidazo[4,5-g]quinazoline-2-one dihydrochloride (Compound 82)

This compound was synthesized from the compound obtained in Reference Example 49.

¹H-NMR(DMSO-d₆) δ(ppm): 1.28(3H, t, J=7.1 Hz), 1.3–1.5(1H, m), 1.65–1.95(5H, m), 2.9–3.1(2H, m), 3.3–3.5 (2H, m), 3.5–3.7(2H, m), 3.95(2H, q, J=7.1 Hz), 4.05–4.2 (2H, m), 7.52(1H, s), 8.19(1H, s), 8.86(1H, s), 10.2–10.35 (1H, m), 10.4–10.6(1H, m), 11.99(1H, s).

EXAMPLE 83

3-ethyl-8-(4-dimethylaminobenzylamino)-2,3-dihydro-1H-imidazo[4,5-g]quinazoline-2-one dihydrochloride (Compound 83)

This compound was synthesized from the compound obtained in Reference Example 50.

¹H-NMR(DMSO-d₆) δ(ppm): 1.26(3H, t, J=7.2 Hz), 3.02 (6H, s), 3.94(2H, q, J=7.2 Hz), 4.90(2H, d, J=5.5 Hz), 7.35–7.52(4H, br), 7.51(1H, s), 8.20(1H, s), 8.81(1H, s), 10.62(1H, br), 12.03(1H, s).

EXAMPLE 84

3-ethyl-8-[α-(2-pyridyl)benzylamino]-2,3-dihydro-1H-imidazo[4,5-g]quinazoline-2-one dihydrochloride (Compound 84)

This compound was synthesized from the compound obtained in Reference Example 51.

¹H-NMR(DMSO-d₆) δ(ppm): 1.31(3H, t, J=7.1 Hz), 4.00 (2H, q, J=7.1 Hz), 7.14(1H, d, J=7.6 Hz), 7.33–7.58(6H, m), 7.80(1H, s), 7.85–8.00(2H, m), 8.62–8.68(2H, m), 8.94(1H, s), 9.17(1H, d, J=5.3 Hz), 10.90(1H, br).

EXAMPLE 85

3-ethyl-8-[1-(2-pyridyl)ethylamino]-2,3-dihydro-1H-imidazo[4,5-g]quinazoline-2-one dihydrochloride (Compound 85)

This compound was synthesized from the compound obtained in Reference Example 52.

¹H-NMR(DMSO-d₆) δ(ppm): 1.32(3H, t, J=7.3 Hz), 1.82 (3H, d, J=7.3 Hz), 3.97(2H, q, J=7.3 Hz), 5.90–5.97(1H, m), 7.51(1H, s), 7.64–7.71(1H, m), 7.86–7.90(1H, m), 8.17–8.23(1H, m), 8.42(1H, s), 8.73(1H, s), 8.74(1H, d, J=3.6 Hz), 10.26(1H, d, J=6.3 Hz), 12.04(1H, s).

EXAMPLE 86

3-ethyl-8-[1-(3-pyridyl)ethylamino]-2,3-dihydro-1H-imidazo[4,5-g]quinazoline-2-one dihydrochloride (Compound 86)

This compound was synthesized from the compound obtained in Reference Example 53.

$^1$H-NMR(DMSO-d$_6$) δ(ppm): 1.28(3H, t, J=6.9 Hz), 1.78 (3H, d, J=6.9 Hz), 3.95(2H, q, J=6.9 Hz), 5.88–5.93(1H, m), 7.52(1H, s), 7.91(1H, dd, J=5.4, 7.9 Hz), 8.39(1H, s), 8.56(1H, d, J=7.9 Hz), 8.77(1H, s), 8.79(1H, s), 9.03 (1H, s), 10.31(1H, d, J=6.9 Hz), 12.06(1H, s).

EXAMPLE 87

3ethyl-8-{3-[4-(2-pyridyl)piperazinyl]propylamino}-2,3-dihydro-1H-imidazo[4,5-g]quinazoline-2-one trihydrochloride (compound 87)

This compound was synthesized from the compound obtained in Reference Example 54.

$^1$H-NMR(DMSO-d$_6$) δ(ppm): 1.27(3H, t, J=6.9 Hz), 2.15–2.30(2H, m), 3.05–3.30(4H, m), 3.45–4.20(8H, m), 4.35–4.55(2H, m), 6.88–6.93(1H, m), 7.21(1H, d, J=8.4 Hz), 7.53(1H, s), 7.80–7.90(1H, m), 8.13(1H, d, J=5.0 Hz), 8.17 (1H, s), 8.83(1H, s), 10.26(1H, br), 11.48(1H, br), 12.02(1H, s).

EXAMPLE 88

3-ethyl-8-(4-morpholinobutylamino)-2,3-dihydro-1H-imidazo[4,5-g]quinazoline-2-one (Compound 88)

This compound was synthesized from the compound obtained in Reference Example 55.

$^1$H-NMR(DMSO-d$_6$) δ(ppm): 1.24(3H, t, J=7.1 Hz), 1.45–1.71(4H, m), 2.27–2.32(6H, m), 3.51–3.57(6H, m), 3.91(2H, q, J=7.1 Hz), 7.32(1H, s), 7.77(1H, s), 7.95–7.99 (1H, m), 8.33(1H, s), 11.36(1H, s).

EXAMPLE 89

3-ethyl-8-[2-(2-methylpiperidino)ethylamino]-2,3-dihydro-1H-imidazo[4,5-g]quinazoline-2-one dihydrochloride (Compound 89)

This compound was synthesized from the compound obtained in Reference Example 56.

$^1$H-NMR(DMSO-d$_6$) δ(ppm): 1.18–1.33(6H, m), 1.65–1.90(4H, m), 2.05–2.25(2H, m), 2.80–2.95(1H, m), 3.00–3.20(2H, m), 3.30–3.50(2H, m), 3.70–4.00(4H, m), 7.61(1H, s), 8.28(1H, s), 8.80(1H, s), 10.46(1H, br), 10.86 (1H, br), 12.04(1H, s).

EXAMPLE 90

3-ethyl-8-(3-morpholinopropylamino)-2,3-dihydro-1H-imidazo[4,5-g]quinazoline-2-thione dihydrochloride (Compound 90)

This compound was synthesized from the compound obtained in Reference Example 43.

$^1$H-NMR(DMSO-d$_6$) δ(ppm): 1.30(3H, t, J=7.2 Hz), 2.1–2.3(2H, m), 2.9–3.3(6H, m), 3.7–4.0(6H, m), 4.35(2H, q, J=7.2 Hz), 7.67(1H, s), 8.20(1H, s), 8.86(1H, s), 10.1–10.2(1H, br), 11.0–11.1(1H, br), 13.74(1H, s).

EXAMPLE 91

3-ethyl-8-(2-morpholinoethylamino)-2,3-dihydro-1H-imidazo[4,5-g]quinazoline-2-thione dihydrochloride (Compound 91)

This compound was synthesized from the compound obtained in Reference Example 44.

$^1$H-NMR(DMSO-d$_6$) δ(ppm): 1.31(3H, t, J=6.9 Hz), 3.3–3.6(6H, m), 3.8–4.0(4H, m), 4.05–4.2(2H, m), 4.36(2H, q, J=6.9 Hz), 7.71(1H, s), 8.33(1H, s), 8.90(1H, s), 10.25–10.35(1H, m), 11.0–11.3(1H, br), 13.25(1H, s).

EXAMPLE 92

3-ethyl-8-[2-(3-pyridyl)ethylamino]-2,3-dihydro-1H-imidazo[4,5-g]quinazoline-2-thione dihydrochloride (Compound 92)

This compound was synthesized from the compound obtained in Reference Example 45.

$^1$H-NMR(DMSO-d$_6$) δ(ppm): 1.30(3H, t, J=7.1 Hz), 3.26 (2H, t, J=6.4 Hz), 4.0–4.2(2H, m), 4.34(2H, q, J=7.1 Hz), 7.76(1H, s), 7.91(1H, dd, J=7.9, 5.6 Hz), 8.31(1H, s), 8.44(1H, d, J=7.9 Hz), 8.77(1H, d, J=5.6 Hz), 8.83(1H, s), 8.90(1H, s), 10.35–10.45(1H, m), 13.73(1H, s).

EXAMPLE 93

3-ethyl-8-[2-(2-pyridyl)ethylamino]-2,3-dihydro-1H-imidazo[4,5-g]quinazoline-2-thione dihydrochloride (Compound 93)

This compound was synthesized from the compound obtained in Reference Example 46.

$^1$H-NMR(DMSO-d$_6$) δ(ppm): 1.31(3H, t, J=7.1 Hz), 3.4–3.6(2H, m), 4.15–4.25(2H, m), 4.35(2H, q, J=7.1 Hz), 7.72(1H, s), 7.75–7.8(1H, m), 7.86(1H, d, J=7.9 Hz), 8.23 (1H, s), 8.25–8.35(1H, m), 8.74(1H, d, J=4.9 Hz), 8.80(1H, s), 10.3–10.4(1H, m), 13.71(1H, s).

EXAMPLE 94

3-ethyl-8-[2-(4-pyridyl)ethylamino]-2,3-dihydro-1H-imidazo[4,5-g]quinazoline-2-thione dihydrochloride (Compound 94)

This compound was synthesized from the compound obtained in Reference Example 47.

$^1$H-NMR(DMSO-d$_6$) δ(ppm): 1.31(3H, t, J=7.1 Hz), 3.3–3.4(2H, m), 4.1–4.2(2H, m), 4.36(2H, q, J=7.1 Hz), 7.72(1H, s), 7.91(2H, d, J=6.3 Hz), 8.28(1H, s), 8.78(2H, d, J=6.3 Hz), 8.86(1H, s), 10.25–10.35(1H, m), 13.73(1H, s).

EXAMPLE 95

3-ethyl-8-[2-(1-pyrrolidinyl)ethylamino]-2,3-dihydro-1H-imidazo[4,5-g]quinazoline-2-thione dihydrochloride (Compound 95)

This compound was synthesized from the compound obtained in Reference Example 48.

$^1$H-NMR(DMSO-ds) δ(ppm): 1.32(3H, t, J=7.0 Hz), 1.8–2.1(4H, m), 3.0–3.2(2H, m), 3.45–3.65(2H, m), 3.65–3.85(2H, m), 4.0–4.2(2H, m), 4.36(2H, q, J=7.0 Hz), 7.73(1H, s), 8.34(1H, s), 8.88(1H, s), 10.2–10.35(1H, m), 10.7–10.9(1H, m), 13.73(1H, s).

EXAMPLE 96

3-ethyl-g-(2-piperidinoethylamino)-2,3-dihydro-1H-imidazo[4,5-g]quinazoline-2-thione dihydrochloride (Compound 96)

This compound was synthesized from the compound obtained in Reference Example 49.

$^1$H-NMR(DMSO-d$_6$) δ(ppm): 1.32(3H, t, J=7.0 Hz), 1.3–1.5(1H, m), 1.65–1.95(5H, m), 2.9–3.1(2H, m), 3.3–3.5

(2H, m), 3.5–3.7(2H, m), 4.1–4.2(2H, m), 4.35(2H, q, J=7.0 Hz), 7.76(1H, s), 8.39(1H, s), 8.90(1H, s), 10.4–10.5 (1H, m), 10.5–10.65(1H, m), 13.74(1H, s).

EXAMPLE 97

3-ethyl-8-(4-dimethylaminobenzylamino)-2,3-dihydro-1H-imidazo[4,5-g]quinazoline-2-thione dihydrochloride (Compound 97)

This compound was synthesized from the compound obtained in Reference Example 50.

$^1$H-NMR(DMSO-$d_6$) δ(ppm): 1.30(3H, t, J=6.9 Hz), 3.04 (6H, s), 4.33(2H, q, J=6.9 Hz), 4.93(2H, d, J=5.4 Hz), 7.54(4H, br), 7.78(1H, s), 8.44(1H, s), 8.86(1H, s), 10.90 (1H, br), 13.79(1H, s).

EXAMPLE 98

3-ethyl-8-[α-(2-pyridyl)benzylamino]-2,3-dihydro-1H-imidazo[4,5-g]quinazoline-2-thione dihydrochloride (Compound 98)

This compound was synthesized from the compound obtained in Reference Example 51.

$^1$H-NMR(DMSO-$d_6$) δ(ppm): 1.30(3H, t, J=7.1 Hz), 4.36 (2H, q, J=7.1 Hz), 7.12(1H, d, J=7.6 Hz), 7.32–7.56(7H, m), 7.75(1H, s), 7.93–7.98(1H, m), 8.66(1H, s), 8.67(1H, d, J=3.3 Hz), 8.89(1H, s), 10.75(1H, d, J=7.6 Hz), 13.78(1H, s).

EXAMPLE 99

3-ethyl-8-[1-(2-pyridyl)ethylamino]-2,3-dihydro-1H-imidazo[4,5-g]quinazoline-2-thione dihydrochloride (Compound 99)

This compound was synthesized from the compound obtained in Reference Example 52.

$^1$H-NMR(DMSO-$d_6$) δ(ppm): 1.34(3H, t, J=7.1 Hz), 1.84 (3H, d, J=6.6 Hz), 4.20–4.40(2H, m), 5.85–6.05(1H, m), 7.66–7.92(3H, m), 8.15–8.25(1H, m), 8.64–8.79(3H, m), 10.51(1H, br), 13.76(1H, s).

EXAMPLE 100

3-ethyl-8-[1-(3-pyridyl)ethylamino]-2,3-dihydro-1H-imidazo[4,5-g]quinazoline-2-thione dihydrochloride (Compound 100)

This compound was synthesized from the compound obtained in Reference Example 53.

$^1$H-NMR(DMSO-$d_6$) δ(ppm): 1.30(3H, t, J=6.9 Hz), 1.81 (3H, d, J=6.9 Hz), 4.35(2H, q, J=6.9 Hz), 5.92–5.97(1H, m), 7.79(1H, s), 8.02–8.08(1H, m), 8.62(1H, s), 8.72(1H, d, J=8.4 Hz), 8.85(1H, s), 8.86(1H, s), 9.10(1H, s), 10.60(1H, d, J=7.4 Hz), 13.84(1H, s).

EXAMPLE 101

3-ethyl-8-{3-[4-(2-pyridyl)piperazinyl]propylamino}-2,3-dihydro-1H-imidazo[4,5-g]quinazoline-2-thione trihydrochloride (Compound 101)

This compound was synthesized from the compound obtained in Reference Example 54.

$^1$H-NMR(DMSO-$d_6$) δ(ppm): 1.30(3H, t, J=7.2 Hz), 2.20–2.30(2H, m), 3.10–3.30(4H, m), 3.45–4.00(6H, m), 4.30–4.55(4H, m), 6.91–6.96(1H, m), 7.26(1H, d, J=8.9 Hz), 7.78(1H, s), 7.87–7.93(1H, m), 8.11(1H, d, J=1.5 Hz), 8.39 (1H, s), 8.88(1H, s), 10.48(1H, br), 11.62(1H, br), 13.79(1H, s).

EXAMPLE 102

3-ethyl-8-(4-morpholinobutylamino)-2,3-dihydro-1H-imidazo[4,5-g]quinazoline-2-thione dihydrochloride (Compound 102)

This compound was synthesized from the compound obtained in Reference Example 55.

$^1$H-NMR(DMSO-$d_6$) δ(ppm): 1.20–1.40(3H, m), 1.65–1.90(4H, m), 2.90–3.60(8H, m), 3.60–4.00(4H, m), 4.20–4.40(2H, m), 7.76(1H, s), 8.41(1H, s), 8.85(1H, s), 10.38(1H, br), 13.74(1H, br).

EXAMPLE 103

3-ethyl-8-(3-imidazolylpropylamino)-2,3-dihydro-1H-imidazo[4,5-g]quinazoline-2-thione dihydrochloride (Compound 103)

Triethylamine (10 ml, 71.7 mmol) and 1-(3-aminopropyl)imidazole (5 ml, 41.9 mmol) were added to a tetrahydrofuran solution (10 ml) of 4-chloro-7--ethylamino-6-nitroquinazoline obtained from 7-ethylamino-6-nitro-4(3H)-quinazolone (610.3 mg, 2.61 mmol) in Reference Example 13 under ice-cooling. The mixture was stirred at room temperature for 19 hours and at 50° C. for 12 hours. After the solvent was distilled off, the residue was purified by silica gel column chromatography (elution with chloroform:methanol=30:1) to give Solid A (800 mg, 89.9%).

To a solution of the resulting Solid A (1.84 g) in a mixed solvent of ethanol (30 ml) and tetrahydrofuran (20 ml), was added a suspension of 10%-palladium on carbon-(200 mg) in water (5 ml) and the mixture was stirred at 40° C. for 4 hours under hydrogen stream. The reaction mixture was filtered with a filter aid and the filtrate was evaporated. To a solution of the residue in ethanol (30 ml), were added triethylamine (1.7 ml, 12.2 mmol) and carbon disulfide (10 ml) and the mixture was stirred at room temperature overnight. After the solvent was distilled off, the residue was purified by silica gel column chromatography (elution with chloroform:methanol=30:1) to give a free base (290 mg, 15.2%) of the title compound. After an excess saturated hydrogen chloride/ethyl acetate solution was added to a suspension of the resulting compound in ethanol to give a uniform solution, the solvent was distilled off. The residue was recrystallized from ethanol to give the title compound.

$^1$H-NMR(DMSO-$d_6$) δ(ppm): 1.30(3H, t, J=7.1 Hz), 2.30 (2H, m), 3.65–3.75(2H, m), 4.25–4.37(4H, m), 7.69(1H, s), 7.79(1H, s), 7.88(1H, s), 8.47(1H, s), 8.82(1H, s), 9.29(1H, s), 10.53(1H, s), 13.77(1H, s).

EXAMPLE 104

3-ethyl-8-(3-dimethylaminopropylamino)-2,3-dihydro-1H-imidazo[4,5-g]quinazoline-2-thione dihydrochloride (Compound 104)

This compound was synthesized from the compound obtained in Reference Example 57.

$^1$H-NMR(DMSO-$d_6$) δ(ppm): 1.30(3H, t, J=7.1 Hz), 2.08–2.13(2H, m), 2.74(3H, s), 2.76(3H, s), 3.14–3.18(2H, m), 3.73–3.80(2H, m), 4.35(2H, q, J=7.1 Hz), 7.71(1H, s),

EXAMPLE 105

3-ethyl-8-[2-(1-methyl-2-pyrrolidinyl)ethylamino]-2,
3-dihydro-1H-imidazo[4,5-g]quinazoline-2-thione
dihydrochloride (Compound 105)

This compound was synthesized from the compound obtained in Reference Example 58.

$^1$H-NMR(DMSO-d$_6$) δ(ppm): 1.30(3H, t, J=7.2 Hz), 1.66–2.20(3H, m), 2.33–2.50(2H, m), 2.75(3H, s), 2.93–3.08(1H, m), 3.23–3.60(3H, m), 3.65–3.83(2H, m), 4.34(2H, q, J=7.2 Hz), 7.78(1H, s), 8.42(1H, s), 8.87(1H, s), 10.40–10.52(1H, br), 10.97–11.10(1H, br), 13.78(1H, s).

EXAMPLE 106 ethyl-8-(3-diethylaminopropylamino)-2,3-dihydro-
1H-imidazo[4,5-g]quinazoline-2-thione
dihydrochloride (Compound 106)

This compound was synthesized from the compound obtained in Reference Example 59.

$^1$H-NMR(DMSO-d$_6$) δ(ppm): 1.10–1.46(9H, m), 2.05–2.25(2H, m), 2.95–3.25(6H, m), 3.60–4.00(2H, m), 4.20–4.40(2H, m), 7.80(1H, s), 8.43(1H, s), 8.86(1H, s), 10.53(1H, br), 10.76(1H, br), 13.78(1H, s).

EXAMPLE 107

3-ethyl-8-{4-[4-(4-methoxyphenyl)piperazinyl]
butylamino}-2,3-dihydro-1H-imidazo[4,5-g]
quinazoline-2-thione trihydrochloride (Compound 107)

This compound was synthesized from the compound obtained in Reference Example 60.

$^1$H-NMR(DMSO-d$_6$) δ(ppm): 1.30(3H, t, J=6.9 Hz), 1.78–1.90(4H, m), 3.15–3.32(6H, m), 3.55–3.77(6H, m), 3.71(3H, s), 4.34(2H, q, J=6.9 Hz), 6.89(2H, d, J=9.2 Hz), 7.04(2H, d, J=9.2 Hz), 7.79(1H, s), 8.44(1H, s), 8.86(1H, s), 10.48(1H, br), 11.37(1H, br), 13.78(1H, s).

EXAMPLE 108

8-[(1-benzyl-4-piperidinyl)methylamino]-3-ethyl-2,
3-dihydro-1H-imidazo[4,5-g]quinazoline-2-thione
dihydrochloride (Compound 108)

This compound was synthesized from the compound obtained in Reference Example 61.

$^1$H-NMR(DMSO-d$_6$) δ(ppm): 1.29(3H, t, J=6.9 Hz), 1.65–2.10(4H, m), 2.80–3.00(2H, m), 3.25–3.55(3H, m), 3.60–3.70(2H, m), 4.25(2H, d, J=4.0 Hz), 4.34(2H, q, J=6.9 Hz), 7.43–7.49(3H, m), 7.60–7.65(2H, m), 7.75(1H, s), 8.38(1H, s), 8.84(1H, s), 10.35(1H, br), 11.01(1H, br), 13.77(1H, s).

EXAMPLE 109

3-ethyl-8-{3-[4-(2-pyrimidyl)piperazinyl]
propylamino}-2,3-dihydro-1H-imidazo[4,5-g]
quinazoline-2-thione trihydrochloride (Compound 109)

This compound was synthesized from the compound obtained in Reference Example 62.

$^1$H-NMR(DMSO-d$_6$) δ(ppm): 1.30(3H, t, J=7.1 Hz), 2.19–2.30(2H, m), 2.95–3.10(2H, m), 3.15–3.30(2H, m), 3.40–3.85(6H, m), 4.35(2H, q, J=7.1 Hz), 4.67–4.73(2H, m), 6.74–6.77(1H, m), 7.74(1H, s), 8.35(1H, s), 8.43–8.45(2H, m), 8.88(1H, s), 10.40(1H, br), 11.30(1H, br), 13.77(1H, br).

EXAMPLE 110 ethyl-8-(3-thiomorpholinopropylamino)-2,3-
dihydro-1H-imidazo[4,5-g]quinazoline-2-thione
dihydrochloride (Compound 110)

This compound was synthesized from the compound obtained in Reference Example 63.

$^1$H-NMR(DMSO-d$_6$) δ(ppm): 1.30(3H, t, J=7.2 Hz), 2.13–2.30(2H, m), 2.73–2.95(2H, m), 3.05–3.60(8H, m), 3.70–3.85(2H, m), 4.35(2H, q, J=7.2 Hz), 7.74(1H, s), 8.35(1H, s), 8.87(1H, s), 10.37(1H, br), 11.22(1H, br), 13.77(1H, s).

EXAMPLE 111

3-ethyl-8-[3-(2,6-dimethylmorpholino)propylamino]
-2,3-dihydro-1H-imidazo[4,5-g]quinazoline-2-thione
dihydrochloride (Compound 111)

This compound was synthesized from the compound obtained in Reference Example 64.

$^1$H-NMR(DMSO-d$_6$) δ(ppm): 1.12(6H, d, J=6.4 Hz), 1.30 (3H, t, J=6.9 Hz), 2.15–2.30(2H, m), 2.45–2.70(2H, m), 3.10–3.50(5H, m), 3.70–3.85(2H, m), 3.90–4.10(1H, m), 4.35(2H, q, J=6.9 Hz), 7.74(1H, s), 8.34(1H, s), 8.87(1H, s), 10.38(1H, br), 11.42(1H, br), 13.78(1H, s).

EXAMPLE 113

3-ethyl-8-(4-thiomorpholinobutylamino)-2,3-
dihydro-1H-imidazo[4,5-g]quinazoline-2-thione
(Compound 112)

This compound was synthesized from the compound obtained in Reference Example 65.

$^1$H-NMR(DMSO-d$_6$) δ(ppm): 1.29(3H, t, J=7.1 Hz), 1.42–1.70(4H, m), 2.35(2H, t, J=7.1 Hz), 2.52–2.60(8H, m), 3.40–3.51(2H, m), 4.34(2H, q, J=7.1 Hz), 7.60(1H, s), 8.03(1H, s), 8.20–8.28(1H, m), 8.38(1H, s).

EXAMPLE 113

3-ethyl-8-(5-thiomorpholinopentylamino)-2,3-
dihydro-1H-imidazo[4,5-g]quinazoline-2-one
(Compound 113)

This compound was synthesized from the compound obtained in Reference Example 67.

$^1$H-NMR(DMSO-d$_6$) δ(ppm): 1.24(3H, t, J=7.2 Hz), 1.24–1.50(4H, m), 1.55–1.70(2H, m), 2.28(2H, t, J=7.2 Hz), 2.52–2.63(8H, m), 3.47–3.54(2H, m), 3.91(2H, q, J=7.2 Hz), 7.31(1H, s), 7.76(1H, s), 7.95–7.99(1H, m), 8.32(1H, s).

EXAMPLE 114

3-ethyl-8-(5-thiomorpholinopentylamino)-2,3-
dihydro-1H-imidazo[4,5-g]quinazoline-2-thione
(Compound 114)

This compound was synthesized from the compound obtained in Reference Example 67.

$^1$H-NMR(DMSO-d$_6$) δ(ppm): 1.28(3H, t, J=6.9 Hz), 1.30–1.50(4H, m), 1.60–1.70(2H, m), 2.28(2H, t, J=6.9 Hz), 2.50–2.70(8H, m), 3.50–3.60(2H, m), 4.34(2H, q, J=6.9 Hz), 7.59(1H, s), 8.02(1H, s), 8.23–8.27(1H, m), 8.37(1H, s), 13.23(1H, br).

EXAMPLE 115

3-ethyl-8-[5-(2,6-dimethylmorpholino)pentylamino]-
2,3-dihydro-1H-imidazo[4,5-g]quinazoline-2-thione
dihydrochloride (Compound 115)

This compound was synthesized from the compound obtained in Reference Example 68.

$^1$H-NMR(DMSO-d$_6$) δ(ppm): 1.12(6H, d, J=6.3 Hz), 1.31 (3H, t, J=7.1 Hz), 1.30–1.50(2H, m), 1.67–1.90(4H, m), 2.50–2.65(2H, m), 2.90–3.05(2H, m), 3.30–3.45(2H, m), 3.70–3.80(2H, m), 3.80–4.10(2H, m), 4.34(2H, q, J=7.1 Hz), 7.76(1H, s), 8.40(1H, s), 8.86(1H, s), 10.36(1H, s), 11.53 (1H, s), 13.76(1H, s).

Effects of the invention

According to the present invention, there are provided imidazoquinazoline derivatives or pharmacologically acceptable salts thereof which have the strong and selective cGMp-specific PDE inhibitory activity and are useful for treating or ameliorating heart diseases such as thrombosis, angina pectoris, hypertension, heart failure, arterial sclerosis and the like, as well as asthma and the like.

We claim:

1. Imidazoquinazoline derivatives represented by the formula (I):

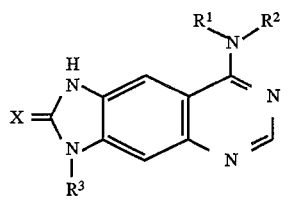

wherein $R^1$ and $R^2$ are the same or different and represent hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, bicycloalkyl, benzocycloalkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl and where said alkyl part is optionally substituted with aryl), aromatic heterocycle group (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen, or trifluoromethyl), or $R^1$—N—$R^2$ represents heterocyclic group comprising nitrogen atom (which is optionally substituted with one to three substituents which are the same or different and are lower alkyl, aryl, or aralkyl), $R^3$ represents hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (where said aromatic heterocycle group part is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl, and where the alkyl part is optionally substituted with aryl), aromatic heterocycle group (where said aromatic heterocycle group is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen, or trifluoromethyl), and X represents sulfur atom, or pharmacologically acceptable salts thereof.

2. Imidazoquinazoline derivatives represented by the formula (I):

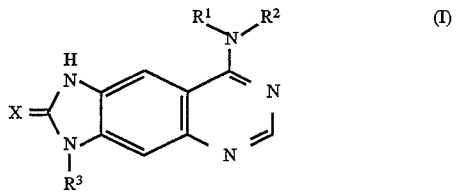

wherein $R^1$ and $R^2$ are the same or different and represent hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, bicycloalkyl, benzocycloalkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl and where said alkyl part is optionally substituted with aryl), aromatic heterocycle group (which is optionally substituted with one to three substituents which are the same or different and are lower alkyl, hydroxy, lower alkoxy, carboxy, lower alkoxy-carbonyl, amino, monoalkyl-substituted amino, dialkyl-substituted-amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen, or trifluoromethyl), or $R^1$—N—$R^2$ taken together represent a 5 to 7-member heterocyclic ring, wherein the members of the heterocyclic ring consist of one or two nitrogen atoms, 4 to 6 carbon atoms, oxygen and sulfur (wherein the heterocyclic ring is optionally substituted with one to three substituents which are the same or different and are lower alkyl, aryl, or aralkyl), $R^3$ represents hydrogen, lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocycle group)), cycloalkyl, lower alkenyl, aryl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), aromatic heterocycle group-substituted alkyl (where said aromatic heterocycle group part is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen or trifluoromethyl, and where the alkyl part is optionally substituted with aryl), aromatic heterocycle group (where said aromatic heterocycle group is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl), or aralkyl (where the aryl part of said aralkyl is optionally substituted with one to three substituents which are the same or different and are lower alkyl, lower alkoxy, dialkyl-substituted amino, halogen or trifluoromethyl), and X represents oxygen atom or sulfur atom, with the proviso that when one of $R^1$ or $R^2$ is hydrogen or unsubstituted alkyl, the other is not substituted or unsubstituted phenyl, or pharmacologically acceptable salts thereof.

3. The imidazoquinazoline derivatives or pharmacologically acceptable salts thereof according to claim 2, wherein X is sulfur atom.

4. The imidazoquinazoline derivatives or pharmacologically acceptable salts thereof according to claim 1, 2 or 3 wherein $R^1$ is lower alkyl (which is optionally substituted with one to three substituents which are the same or different and are cycloalkyl, hydroxy, lower alkoxy, carboxy, lower alkoxycarbonyl, amino, monoalkyl-substituted amino, dialkyl-substituted amino, nitro, halogen, or alicyclic heterocycle group (which is optionally substituted with one to three substituents which are the same or different and are lower alkyl, aralkyl, aryl optionally substituted with one to three substituents which are the same or different and are lower alkoxy, or aromatic heterocyclic group)), aromatic heterocycle group-substituted alkyl (which is optionally substituted with one to three substituents which are the same or different and are lower alkyl, hydroxy, lower alkoxy, carboxy, lower alkoxycarbonyl, amino, monoalkyl-substituted amino, dialkyl-substituted amino, nitro, sulfonamide, halogen, or trifluoromethyl, and where the alkyl part is optionally substituted with aryl), or aralkyl (where the aryl part of said aralkyl is optionally substituted with one to three substituents which are the same or different and are lower alkyl, lower alkoxy, dialkyl-substituted amino, halogen, or trifluoromethyl), and $R^2$ is hydrogen.

5. The imidazoquinazoline derivatives or pharmacologically acceptable salts thereof according to claim 1, 2 or 3, wherein $R^3$ is lower alkyl.

6. A pharmaceutical composition which comprises a pharmacologically acceptable carrier and the imidazoquinazoline derivatives or pharmacologically acceptable salts thereof according to claim 1, 2 or 3.

7. A pharmaceutical composition which comprises a pharmacologically acceptable carrier and the imidazoquinazoline derivatives or pharmacologically acceptable salts thereof according to claim 4.

8. A pharmaceutical composition which comprises a pharmacologically acceptable carrier and the imidazoquinazoline derivatives or pharmacologically acceptable salts thereof according to claim 5.

\* \* \* \* \*

UNITED STATES PATENT AND TRADEMARK OFFICE
CERTIFICATE OF CORRECTION

PATENT NO. : 5,661,147

DATED : August 26, 1997

INVENTOR(S): DAISUKE MACHII ET AL.

It is certified that error appears in the above-identified patent and that said Letters Patent is hereby corrected as shown below:

COLUMN 2

Line 9, "be" should be deleted.

COLUMN 5

Line 62, "liked" should read --like,--.

COLUMN 6

Line 18, "salt,.which" should read --salt, which--.

COLUMN 21

Line 25, "[$^3$H]Adenosine" should read --[$^3$H]Adenosine or--.

COLUMN 23

Line 38, "hu 1H-NMR(DMSO-d$_6$," should read --$^1$H-NMR(DMSO-d$_6$,--;

Line 49, "$^1$H-NMR" should read --¶ $^1$H-NMR--.

UNITED STATES PATENT AND TRADEMARK OFFICE
CERTIFICATE OF CORRECTION

PATENT NO. : 5,661,147

DATED : August 26, 1997

INVENTOR(S): DAISUKE MACHII ET AL.

It is certified that error appears in the above-identified patent and that said Letters Patent is hereby corrected as shown below:

COLUMN 40

Line 17, "8—cyclohexylmethyl$^{amino}$—3—" should read --8—cyclohexylmethylamino—3---

COLUMN 47

Line 54, "8.00(1H,s)f" should read --8.00(1H,s),--.

COLUMN 53

Line 19, "ethyl—8—" should read --3—ethyl—8---.

COLUMN 54

Line 6, "ethyl—8—" should read --3—ethyl—8---;

Line 31, "EXAMPLE 113" should read --EXAMPLE 112--.

COLUMN 55

Line 18, "cGMp-specific" should read --cGMP-specific--.

UNITED STATES PATENT AND TRADEMARK OFFICE
CERTIFICATE OF CORRECTION

PATENT NO. : 5,661,147

DATED : August 26, 1997

INVENTOR(S): DAISUKE MACHII ET AL.

It is certified that error appears in the above-identified patent and that said Letters Patent is hereby corrected as shown below:

COLUMN 56

Line 5, "represents" should read --taken together represent a 5 to 7-member--;

Line 6, "group comprising nitrogen atom" should read --ring, wherein the members of the heterocyclic ring consist of one or two nitrogen atoms, 4 to 6 carbon atoms, oxygen and sulfur--.

Signed and Sealed this

Fourteenth Day of July, 1998

Attest:

BRUCE LEHMAN

Attesting Officer        Commissioner of Patents and Trademarks